US008017755B2

(12) United States Patent
Liu et al.

(10) Patent No.: US 8,017,755 B2
(45) Date of Patent: Sep. 13, 2011

(54) RNA-BASED TRANSCRIPTIONAL REGULATORS

(75) Inventors: David R. Liu, Lexington, MA (US);
Allen R. Buskirk, Provo, UT (US);
Polina D. Kehayova, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 2174 days.

(21) Appl. No.: 10/852,626

(22) Filed: May 24, 2004

(65) Prior Publication Data

US 2005/0070016 A1    Mar. 31, 2005

Related U.S. Application Data

(60) Provisional application No. 60/472,876, filed on May 23, 2003.

(51) Int. Cl.
| | |
|---|---|
| *C07H 21/02* | (2006.01) |
| *C07H 21/04* | (2006.01) |
| *C12N 15/00* | (2006.01) |
| *C07K 14/00* | (2006.01) |
| *C07K 14/08* | (2006.01) |
| *C07K 14/195* | (2006.01) |

(52) U.S. Cl. .................... 536/24.1; 536/23.1; 435/320.1; 530/350

(58) Field of Classification Search ........................ None
See application file for complete search history.

(56) References Cited

U.S. PATENT DOCUMENTS

| 6,706,481 | B2 | 3/2004 | Rajendran et al. | |
|---|---|---|---|---|
| 7,285,398 | B2 * | 10/2007 | Fraser | 435/69.1 |
| 2004/0014036 | A1 | 1/2004 | Ptashne et al. | |

FOREIGN PATENT DOCUMENTS

| WO | WO 91/19813 | | 12/1991 |
|---|---|---|---|
| WO | WO 92/05285 | | 4/1992 |
| WO | WO 92/14843 | | 9/1992 |
| WO | WO 99/10487 | | 3/1999 |
| WO | WO 0060075 | A1 * | 10/2000 |
| WO | WO 02/34295 | | 5/2002 |

OTHER PUBLICATIONS

Soukup et al. Nucleic acid molecular switches. Trends in Biotechnology, vol. 17, No. 12, pp. 469-476, Dec. 1999.*
Baugh, et al., "A Crystal Structure of the Malachite Green Aptamer", *J. Mol. Biol.* 301: 117-128, 2000.
Beerli, et al., "Toward Controlling Gene Expression at Will: Specific Regulation of the erbB-2/HER-2 Promoter by Using Polydactyl Zinc Finger Proteins Constructed from Modular Building Blocks", *Proc. Natl. Acad. Sci. USA*, 95: 14628-14633, 1998.
Berg, T., "Modulation of Protein-Protein Interactions with Small Organic Molecules", *Angew. Chem. Int. Ed. Engl.* 42: 2462-2481, 2003.
Bernstein, et al., "Analyzing mRNA-Protein Complexes Using a Yeast Three-Hybrid System", *Methods*, 26: 123-141, 2002.
Blind, et al., "Cytoplasmic RNA Modulators of an Inside-Out Signal-Transduction Cascade", *Proc. Natl. Acad. Sci. USA*, 96: 3606-3610, 1999.

Blum, et al., "Isolation of Peptide Aptamers that Inhibit Intracellular Processes", *Proc. Natl. Acad. Sci USA*, 97: 2241-2246, 2000.
Buskirk, et al., "In Vivo Evolution of an RNA-Based Transcriptional Activator", *Chem. Biol.* 10: 533-540, 2003.
Cassidy, et al., "Yeast Genetic Selections to Optimize RNA Decoys for Transcription Factor NF-Kappa B", *Proc. Natl Acad. Sci. USA*, 100: 3930-3935, 2003.
Doudna, et al., "The Chemical Repertoire of Natural Ribozymes", *Nature*, 418: 222-228, 2002.
Eddy, S.R., "Non-Coding RNA Genes and the Modern RNA World", *Nat. Rev. Genet.* 2: 919-929, 2001.
Famulok, et al., "In Vivo-Applied Functional RNA s as Tools in Proteomics and Genomics Research", *Trends Biotechnol*, 20: 462-466, 2002.
Ferber, et al., "Combinatorial Selection of a Small RNA that Induces Amplification of IncFII Plasmids in *Escherichia coli*", *J. Mol. Biol.* 279: 565-576, 1998.
Geyer, "Mutagenesis" by Peptide Aptamers Identifies Genetic Network Members and Pathway Connections, *Proc.Natl Acad Sci USA*, 96: 8567-8572, 1999.
Good, et al., "Yeast Expression Vectors Using RNA Polymerase III Promotoers", *Gene*, 151: 209-214, 1994.
Grate, et al., "Laser-Mediated, Site-Specific Inactivation of RNA Transcripts", *Proc. Natl. Acad. Sci*, USA, 96: 6131-6136, 1999.
Grate, et al., "Inducible Regulation of the S. Cerevisiae Cell Cycle Mediated by an RNA Aptamer-Ligand Complex", *Bioorg. Med. Chem.* 9: 2565-2570, 2001.
Keefe, et al., "Functional Proteins from a Random-Sequence Library", *Nature*, 410: 715-718, 2001. Lanz, et al., "A Steroid Receptor Coactivator, SRA, Functions as an RNA and Is Present in an SRC-1 Complex", *Cell*, 97: 17-27, 1999.
Lanz, et al., "Distinct RNA Motifs are Important for Coactivation of Steroid Hormone Receptors by Steroid Receptor RNA Activator (SRA)", *Proc. Natl. Acad. Sci*, USA, 99: 16081-16086, 2002.
Lau, et al., "An Abundant Class of Tiny RNAs with Probable Regulatory Roles in *Caenorhabditis elegans*" *Science*, 294: 858-862, 2001.
Lu, et al., "An Artificial Transcriptional Activating Region with Unusual Properties", *Proc. Natl. Acad. Sci. USA*, 97: 1988-1992, 2000.
Ma, et al., "A New Class of Yeast Transcriptional Activators", *Cell*, 51: 113-119, 1987.
Mathews, et al., "Expanded Sequence Dependence of Thermodynamic Parameters Improves Prediction of RNA Secondary Structure", *J. Mol. Biol.* 288: 911-940, 1999.
Moore, et al., "The Involvement of RNA in Ribosome Function", *Nature*, 418, 229-235, 2002.

(Continued)

*Primary Examiner* — Jennifer Dunston
(74) *Attorney, Agent, or Firm* — Wolf, Greenfield & Sacks, P.C.; C. Hunter Baker; Daniel W. Young

(57) ABSTRACT

RNA molecules have been shown to play a variety of functional roles in biological processes. RNA sequences can adopt 3-D conformations able to regulate transcription. RNA-based transcriptional regulators when recruited to a DNA template act to promote or suppress the transcription of nearby genes. The regulators are thought to act by mimicing the activation domains of protein transcriptional activators. These RNA-based transcriptional regulators may be engineered to regulate transcription based on the binding of a ligand such as a small molecule. RNA sequences of the regulators may be evolved to produce regulators with a greater degree of transcriptional activation or suppression. The RNA-based system of the present invention is useful in studying biological processes and in altering biological process in a therapeutic context.

44 Claims, 9 Drawing Sheets

OTHER PUBLICATIONS

Mumberg, et al., "Yeast Vectors for the Controlled Expression of Heterologous Proteins in Different Genetic Backgrounds" *Gene*, 156: 119-122, 1995.

Norman, et al., "Genetic Selection of Peptide Inhibitors of Biological Pathways", *Science*, 285: 591-595, 1999.

Ponticelli, et al., "The Glutamine-Rich Activation Domains of Human Sp1 Do Not Stimulate Transcription in *Saccharomyces cerevisiae*", *Mol. Cell Biol.* 15: 983-988, 1995.

Pryciak, et al., "AKR1 Encodes a Candidate Effector of the Gβγ Complex in the *Saccharomyces cerevisiae* Pheromone Response Pathway and Contributes to Control of Both Cell Shape and Signal Transduction", *Mol. Cell. Biol.* 16: 2614-2626, 1996.

Ptashne, et al., "Transcriptional Activation by Recruitment", *Nature*, 386: 569-577, 1997.

Sadowski, et al., "GAL4-VP16 is an Unusually Potent Transcriptional Activator", *Nature*, 335: 563-564, 1988.

Sengupta, et al., "Identification of RNAs that Bind to a Specific Protein Using the Yeast Three-Hybrid System", *RNA*, 5: 596-601, 1999.

Sengupta, et al., "A Three-Hybrid System to Detect RNA-Protein Interactions in Vivo", *Proc. Natl Acad Sci USA*, 93: 8496-8501, 1996.

Shi, et al., "RNA Aptamers as Effective Protein Antagonists in a Multicellular Organism", *Proc. Natl. Acad. Sci. USA*, 96: 10033-10038, 1999.

Soukup, et al., "Selection and Characterization of RNAs that Relieve Transcriptional Interference in *Escherichia coli*", *Nucleic Acids Res.* 26: 2715-2722, 1998.

Soukup, et al., "Allosteric Nucleic Acid Catalysts", *Curr Opin Struct Biol*, 10: 318-325, 2000.

Soukup, et al., "Altering Molecular Recognition of RNA Aptamers by Allosteric Selection", *J. Mol. Biol.* 298: 623-632, 2000.

Storz, G., "An Expanding Universe of Noncoding RNAs", *Science*, 296: 1260-1263, 2002.

Struhl, K., "Yeast Transcriptional Regulatory Mechanisms", *Annu Rev. Genet.* 29: 651-674, 1995.

Thomas, et al., "Selective Targeting and inhibition of Yeast RNA Polymerase II by RNA Aptamers", *J. Biol. Chem.* 272: 27980-27986, 1997.

Tzamarias, "Functional Dissection of the Yeast Cyc8-Tup1 Transcriptional Co-Repressor Complex", *Nature*, 369: 758-761, 1994.

Vuyisich, et al., "Controlling Protein Activity with Ligand-Regulated RNA Aptamers", *Chem. Biol.* 9: 907-913, 2002.

Wilson, et al., "In Vitro Selection of Functional Nucleic Acids", *Annu. Rev. Biochem.* 68: 611-647, 1999.

Winkler, et al., "Thiamine Derivatives Bind Messenger RNAs Directly to Regulate Bacterial Gene Expression", *Nature*, 419: 952-956, 2002.

Winkler, "Control of Gene Expression by a Natural Metabolite-Responsive Ribozyme", *Nature*, 428: 281-286, 2004.

Zhang, et al., "Yeast Three-Hybrid System to Detect and Analyze RNA-Protein Interactions" *Methods Enzymol*, 318: 399-419, 2000.

Zimmerman, et al., "In Vivo Selection of Spectinomycin-Binding RNAs", *Nucleic Acids Res*, 30: 5425-5435, 2002.

Zuker, M. "Mfold Web Server for Nucleic Acid Folding and Hybridization Prediction", *Nucleic Acids Res*, 31: 3406-3415, 2003.

\* cited by examiner

```
                            1         1         2         2         3         3         4
                   1   5    0         5         0         5         0         5         0
     N40-26        CGCGGAAGAATGCT-CCCCCAAGTGGATGCCTAAGCCTCTT
     m26-10        CGCGGAAGAATGAT-CCCCCAAGTGGATGCCTAAGCCTCTT
     m26-36        CGCGGAAGAATTCT-CCCCCAAGTGGATGCCTAAGCCTCTT
     m26-31        CGCGGAAGAATGCT-CCCCCGAGTGGATGCCTAAGCCTCAT
     m26-9         CGCGGAGGAATGCT-CCCCCGAGTGGATGCCTAATCCTCTT
     m26-14        CGCGGAAGCATACT-CCCCCGAGTGGATGCCTAAGCCTCTT
     m26-15        CGCGGACCAATGGT-CCCCCAAGTGGATGCCTAAGCCTCTT
     m26-34        CGCGGAAGATTGCC-CCCCCAAGTGGATGCCTAAACCTCTA
     m26-29        CGCGGAAGATTGTT-CCCCCAAGTGGATGCCTAAACCTCAT
     m26-28        CGCGGAAAAATACT-CCCCCAAGTGGATGCCTAAACCTATT
     m26-17        CGCGGAAGAATGAT-CCCCCAGGTGGATGCCTAAGCCTCTA
     m26-30        CGCGGAACAATGCT-CCCCCAGCTGGATGCCTAAGCCTCTA
     m26-20        CGGGGAAGAATGCT-GCCCAAAGTGGATGCCTAAGCCTCTT
     m26-4         CGCGGAAGAATGCT-GCCCAACCTGGATGCCTAAACCTCTT
     m26-32        CGCGGAAGAATGCT-GCCCAACCTGGATGCCTAAACCTCTT
     m26-13        CTCGGAACAATGCC-CCCCCAAGTGGATGCCTAAACCTCAT
     m26-35        CTCGGAAGAATTCT-CCCGATAGTGGATGCCTAAGCCTCTT
     m26-16        CGCGGAAGAAGAGT-CCCCCGAGTGGATGCCTAAACCTCTT
     m26-18        CGCGGAACAATGTT-GCCCAAATGGATGCCTAAGCCTCTT
     m26-25        CGCGGAAGAACACT-CCCCCACGTGGATGCCTAAGCCTCCTT
     m26-21        CGCGGAAGACTGCA-GCCCCAGGTGGATGCCTAAACCTCGGT
     m26-39        CCCGGAAGACTGCA-GCCCCAGGTGGATGCCTAAACCTCTT
     m26-33        CGCGGAAGACTTCA-GCCCCAAGTGGATGCCTAAGCCTCTTA
     m26-1         CGCGGGTGTAAGCC-CCCCCAGGTGGATGCCTAAGCCTCTT
     m26-23        CGCGTAAACATGCG-GCCCCAAGTGGATGCCTAAGCCTCCT
     m26-24        CGCGGAAAGATGAT-CACCCGAGTGGATGCCTAAGCCTCTT
     m26-11        CGCGCGAGTATACT-CCCCCAAGCGGATGCCTAAGCCTCTT
     m26-19        CGCAGAAGATACCT-CCCCCAAGTGGATGCCTAAGCCTCAT
     m26-26        AACAGAAGAATACT-CCCCCAAGTGGATACCTAAGCATCTT
     m26-37        CGCGGAAAAATTCTTCCCCCAAGTGGATGCCTAAGCCTCTT
     m26-38        CGCGGAAAAATTCTTCCCCCAAGTGGATGCGTAAGCCTCTT
     m26-7         CGCGGAAGAACGCT-CCCCGACGTGGATGCCTATTGTCCTT
     consensus     CGCGGAAGAATGCT-CCCCCAAGTGGATGCCTAAGCCTCTT
```

Figure 4

A
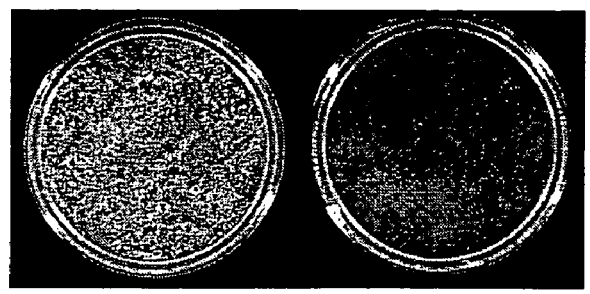
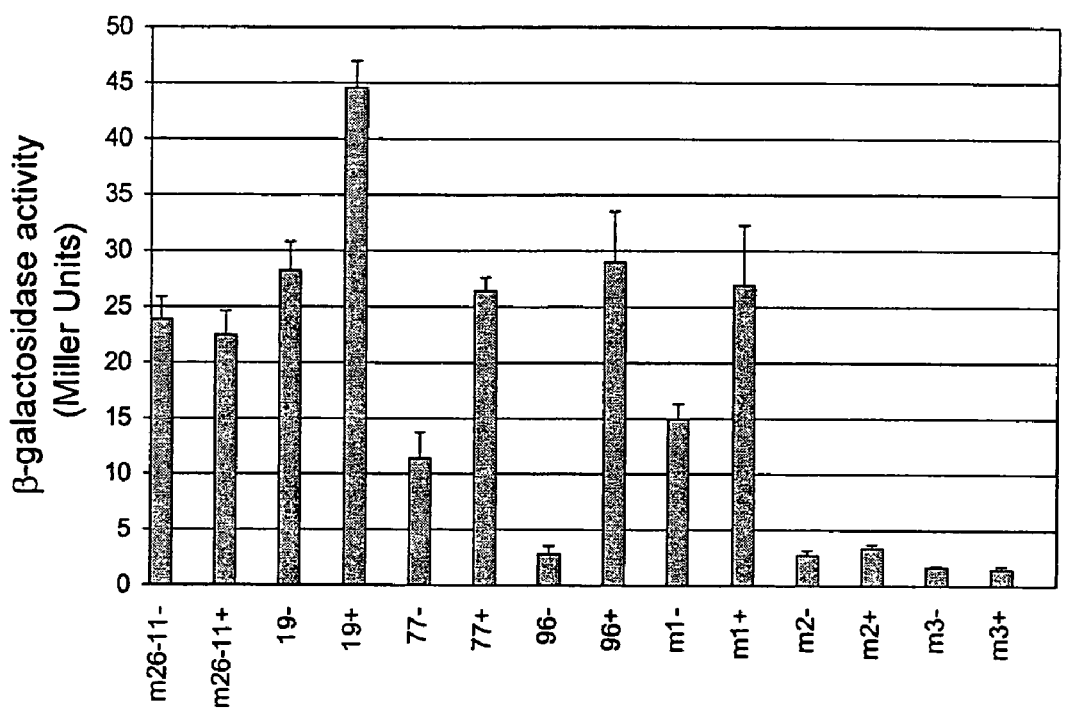
Figure 8

RNA-BASED TRANSCRIPTIONAL REGULATORS

RELATED APPLICATIONS

The present application claims priority to U.S. provisional application, U.S. Ser. No. 60/472,876, filed May 23, 2003, which is incorporated herein by reference in its entirety.

GOVERNMENT SUPPORT

The work described herein was supported, in part, by grants from the National Science Foundation (MCB-0094128) and the National Institutes of Health (1R01GM65400-01). The United States Government has certain rights in the invention

BACKGROUND

In addition to its role as a transient carrier of genetic information within a cell, RNA is now known to play a variety of functional roles in several biological processes including tRNA processing, intron splicing, and peptide-bond formation during translation (Doudna, J. A., and Cech, T. R. (2002). The chemical repertoire of natural ribozymes. Nature 418, 222-228; Moore, P. B., and Steitz, T. A. (2002). The involvement of RNA in ribosome function. Nature 418, 229-235). The recent discovery of a class of small RNAs that block translation by base pairing to the 3'-untranslated region of mRNAs reveals that natural RNAs can also regulate gene expression (Lau, N. C., Lim, L. P., Weinstein, E. G., and Bartel, D. P. (2001). An abundant class of tiny RNAs with probable regulatory roles in *Caenorhabditis elegans*. Science 294, 858-862). O'Malley and co-workers recently discovered an RNA that plays a structural role in a protein-RNA complex that co-activates genes regulated by steroid hormone receptors (Lanz, R. B., McKenna, N. J., Onate, S. A., Albrecht, U., Wong, J., Tsai, S. Y., Tsai, M. J., and O'Malley, B. W. (1999). A steroid receptor coactivator, SRA, functions as an RNA and is present in an SRC-1 complex. Cell 97, 17-27; Lanz, R. B., Razani, B., Goldberg, A. D., and O'Malley, B. W. (2002). Distinct RNA motifs are important for coactivation of steroid hormone receptors by steroid receptor RNA activator (SRA). Proc Natl Acad Sci USA 99, 16081-16086). An RNA molecule that functions as a transcriptional activation domain, however, has not yet been discovered in nature.

The activation of transcription in the nucleus of a cells requires multiple interactions of proteins and DNA at the start site of the gene. Ptashne and co-workers have shown that DNA-bound protein activators are required to recruit other transcription factors to the start site to begin transcription (Ptashne, *Nature* 335:983, 1988). In eukaryotes, for example, activation of RNA polymerase II genes requires many transcription factors in addition to RNA polymerase. Transcriptional activators have been shown to contact one or another of these transcription factors including the TATA-binding protein (TBP), TBP-associated factors (TAFs), TFIIB, and TFIIH (Roeder, *Trends Biochem. Sci.* 16:402, 1991; Zawel et al., *Prog. Nucl. Acids Res. Mol. Biol.* 44:67, 1993; Conaway et al., *Annu. Rev. Biochem.* 62:161, 1993; Hoey et al., *Cell* 72:247). Therefore, the initiation of transcription involves a multistep assembly process of which activators play a key role. (Buratowski et al. *Cell* 56:549, 1989; Choy et al., *Nature* 366:531, 1993). Some transcriptional activators are thought to recruit transcriptional factors to the DNA while others are thought to cause conformational changes in target proteins thereby facilitating the assembly of the transcriptional machinery (Lin et al. *Cell* 64:971, 1991; Roberts et al. *Nature* 371:717, 1994; Hori et al., *Curr. Opin. Genet. Dev.* 4:236, 1994).

Transcriptional activation has been studied both in the context of controlling gene expression in cells, for example so that the principles of gene activation might be employed in genetic therapies, and as an experimental tool for analyzing protein-protein interactions in the cell (Fields et al. *Nature* 340:245, 1989; Gyuris et al., *Cell* 75:791, 1993). There remains a need for novel transcriptional activators, especially ones that are able to be switched on and off.

SUMMARY OF THE INVENTION

The present invention stems from the recognition that RNA is capable of accessing the structural and functional diversity needed to regulate transcription and that this activity can be regulated by the binding of a ligand to the RNA. Particularly, an RNA molecule can mimic the transcriptional activation domain of a protein and thereby regulate the transcription of a gene of interest. In this manner, RNA-based transcriptional regulators may be used to perturb cellular function in both an experimental and clinical setting. In certain preferred embodiments, RNA-based transcriptional regulators may be used to probe the function and mechanism of biological pathways.

RNA-based transcriptional regulators of the present invention act to increase or decrease the transcription of a gene. The regulator is typically recruited to the gene to be transcribed in order to affect transcription of the gene (e.g., upstream of the gene near the transcription start site or promoter). The inventive regulators include an RNA sequence responsible for activation associated with an element that allows recruitment to the DNA template to be transcribed. The 3D structure of the RNA-based transcriptional regulator provides the surface necessary to recruit proteins necessary for transcription and/or to induce changes in proteins of the transcriptional machinery, thereby inducing transcription. In this way, the RNA mimics the structure normally provided by the activation domain of a protein transcriptional activator, which are traditionally thought of as having a DNA-binding domain and an activation domain. The RNA activation domain may be tethered upstream of the gene being regulated by the aid of a protein known to bind DNA through a covalent or non-covalent interaction, preferably non-covalent. For example, the RNA activation sequence of the regulator may be a part of a larger RNA molecule with a known secondary structure (e.g., hairpin loop) known to associate with a DNA-binding protein. In certain embodiments, the RNA-based transcriptional regulator includes a sequence known to interact directly with a DNA binding protein (e.g., a fusion protein with a DNA binding domain and an RNA binding domain) or indirectly through another protein.

The RNA-based transcriptional regulator may also be responsive to the binding of a ligand. For example, binding of the ligand may lead to a conformational change in the regulator that allows it to recruit the transcriptional machinery necessary to initiate transcription of a particular gene. The resulting level of transcription is preferably dependent upon the concentration of ligand present. The ligand can be any chemical compound including metals, small molecules, organic compounds, inorganic compounds, protons or hydronium ions, hydroxide, proteins, peptides, etc. Ligand-dependent RNA-based transcriptional regulators that can be switched on or off via the binding of the ligand are particularly useful in probing biological pathways.

In another aspect, the present invention provides a system for evolving desired RNA-based transcriptional regulators including ligand-dependent regulators. The method of evolving RNA-based transcriptional regulators includes providing a pool of RNA sequences and selecting regulators based on their ability to increase or decrease the transcription of a reporter gene (e.g., β-galactosidase, HIS3, green fluorescent protein (GFP)). The selected regulator sequences are then mutated, and the mutated sequences are reselected for sequences with an even greater ability to increase transcription. The method may be repeated to evolve regulators with a desired ability to increase transcription. In this way, RNA-based transcriptional activators as potent or more potent than natural protein activators may be prepared. An analogous method is used to evolve ligand-dependent RNA-based transcriptional regulators. Sequences designed with a ligand-binding aptamer are mutated and selected based on their ability to be controlled by ligand binding.

The RNA-based transcriptional regulators of the present invention are useful in probing cell function by regulating the expression of a particular gene(s). The regulators are used to investigate biochemical pathways, development, biological pathways, cancer development, and gene expression. The RNA-based transcriptional regulators are typically used in conjunction with a DNA-binding protein known to bind an element of the RNA-based transcriptional regulator, thereby recruiting the RNA to a start site for transcription. The DNA-binding protein may recruit the regulator to a particular gene for controlling the expression of the gene. The regulator may also be used to affect the transcription of set of genes on an operon, a family of genes, or all genes in a genome. The reagents such as plasmids encoding the RNA-based transcriptional regulator, plasmids encoding DNA-binding protein, cell line, buffer, media, reagents, and instructions useful in practicing the present inventive system may be provided in a kit for convenience.

The RNA-based transcriptional regulators are also useful in treating or preventing diseases involving gene expression. Cancer, inflammatory diseases, genetic diseases, autoimmune diseases, infectious diseases including viral diseases, and heart disease are all diseases that can be treated using the inventive RNA-based transcriptional regulators. For delivery of the regulator a vector encoding the RNA regulator is typically used. Any techniques in the art of gene therapy may be used in administering an RNA-based transcriptional activator.

DEFINITIONS

The term aptamer refers to nucleic acid molecules having a tertiary structure which permits them to specifically bind to protein ligands (see, e.g., Osborne, et al. Curr. Opin. Chem Biol. 1997, 1(1): 5-9; and Patel, D. J. Curr Opin Chem Biol June 1997; 1(1):32-46). An aptamer may be a single- or double-stranded DNA or a single-stranded RNA molecule. See, e.g., PCT Publication Nos. WO92/14843, WO91/19813, and WO92/05285, the disclosures of which are incorporated by reference herein.

A ligand refers to any chemical compound, polynucleotide, peptide, protein, lipid, carbohydrate, small molecule, natural product, polymer, etc. that has a binding affinity for a target (e.g., a protein, carbohydrate, lipid, peptide, macromolecules, biological macromolecules, oligonucleotide, polynucleotide). In the present invention, the ligand's target is an RNA-based transcriptional regulator. In some embodiments, the ligand is specific for its target, the RNA-based transcriptional regulator. In some embodiments, the ligand has a binding affinity for the target in the range of 100 mM to 1 pM, preferably 1 mM to 1 pM, more preferably 1 μM to 1 pM, most preferably less than 100 nM. The ligand may bind to its target via any means including hydrophobic interactions, hydrogen bonding, electrostatic interactions, van der Waals interactions, pi stacking, covalent bonding, magnetic interactions, etc.

Polynucleotide or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

A protein comprises a polymer of amino acid residues linked together by peptide (amide) bonds. The term, as used herein, refers to proteins, polypeptides, and peptides of any size, structure, or function. Typically, a protein will be at least three amino acids long, preferably at least 10 amino acids in length, more preferably at least 25 amino acids in length, and most preferably at least 50 amino acids in length. Proteins may also be greater than 100 amino acids in length. A protein may refer to an individual protein or a collection of proteins. A protein may refer to a full-length protein or a fragment of a protein. Proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a myristoyl group, a fatty acid group, a linker for conjugation, functionalization, or other modification, etc. A protein may also be a single molecule or may be a multi-molecular complex comprising proteins, lipids, RNA, DNA, carbohydrates, etc. A protein may be a natural or unnatural fragment of a naturally occurring protein or peptide. A protein may be naturally occurring, recombinant, or synthetic, or any combination of these.

The term small molecule, as used herein, refers to a non-peptidic, non-oligomeric organic compound either synthesized in the laboratory or found in nature. Small molecules, as used herein, can refer to compounds that are "natural product-like", such as small molecules that are similar in structure to a natural product or are similar with respect to density of stereocenters, density of functional groups, ring systems, 3-D structure, etc.; however, the term "small molecule" is not limited to "natural product-like" compounds and may include compounds that are not based on and are not similar to known natural products. Rather, a small molecule is typically characterized in that it contains several carbon-carbon bonds, and has a molecular weight of less than 1500, although this characterization is not intended to be limiting for the purposes of the present invention. Examples of small molecules that occur in nature include, but are not limited to, taxol, dynemicin, cholesterol, and rapamycin.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 4 is an alignment of variable region sequences from evolved N40-26 variants. Sequence N40-26 is SEQ ID NO: 107; m26-10 is SEQ ID NO: 72; m26-36 is SEQ ID NO: 73; m26-31 is SEQ ID NO: 74; m26-9 is SEQ ID NO: 75; m26-14 is SEQ ID NO: 76; m26-15 is SEQ ID NO: 77; m26-34 is SEQ ID NO: 78; m26-29 is SEQ ID NO: 79; m26-28 is SEQ ID NO: 80; m26-17 is SEQ ID NO: 81; m26-30 is SEQ ID NO: 82; m26-20 is SEQ ID NO: 83; m26-4 is SEQ ID NO: 84; m26-32 is SEQ ID NO: 85; m26-13 is SEQ ID NO: 86; m26-35 is SEQ ID NO: 87; m26-16 is SEQ ID NO: 88; m26-18 is SEQ ID NO: 89; m26-25 is SEQ ID NO: 90; m26-21 is SEQ ID NO: 91; m26-39 is SEQ ID NO: 92; m26-33 is SEQ ID NO: 93; m26-1 is SEQ ID NO: 94; m26-33 is SEQ ID NO: 95; m26-24 is SEQ ID NO: 96; m26-11 is SEQ ID NO: 97; m26-19 is SEQ ID NO: 98; m26-26 is SEQ ID NO: 99; m26-37 is SEQ ID NO: 100; m26-38 is SEQ ID NO: 101; m26-7 is SEQ ID NO: 102; and the consensus sequence is SEQ ID NO: 103.

FIG. 8 depict the transcriptional activation and ligand dependence of RNAs in this study. (A) *S. cerevisiae* strain YBZ-1 transformed with clone 96 were plated on media lacking histidine and containing 1 mM 3-AT, a competitive inhibitor of His3p activity. Transcriptional activation of the HIS3 reporter conveys survival on media containing 1 μM TMR (left), but no survival in the absence of TMR (right). (B) Quantitative β-galactosidase assays of lysates from cells expressing various RNAs described in this work grown in the presence or absence of 1 μM TMR. Error bars reflect standard deviations of values from independent assays performed in triplicate.

DETAILED DESCRIPTION OF THE INVENTION

Figure 1:
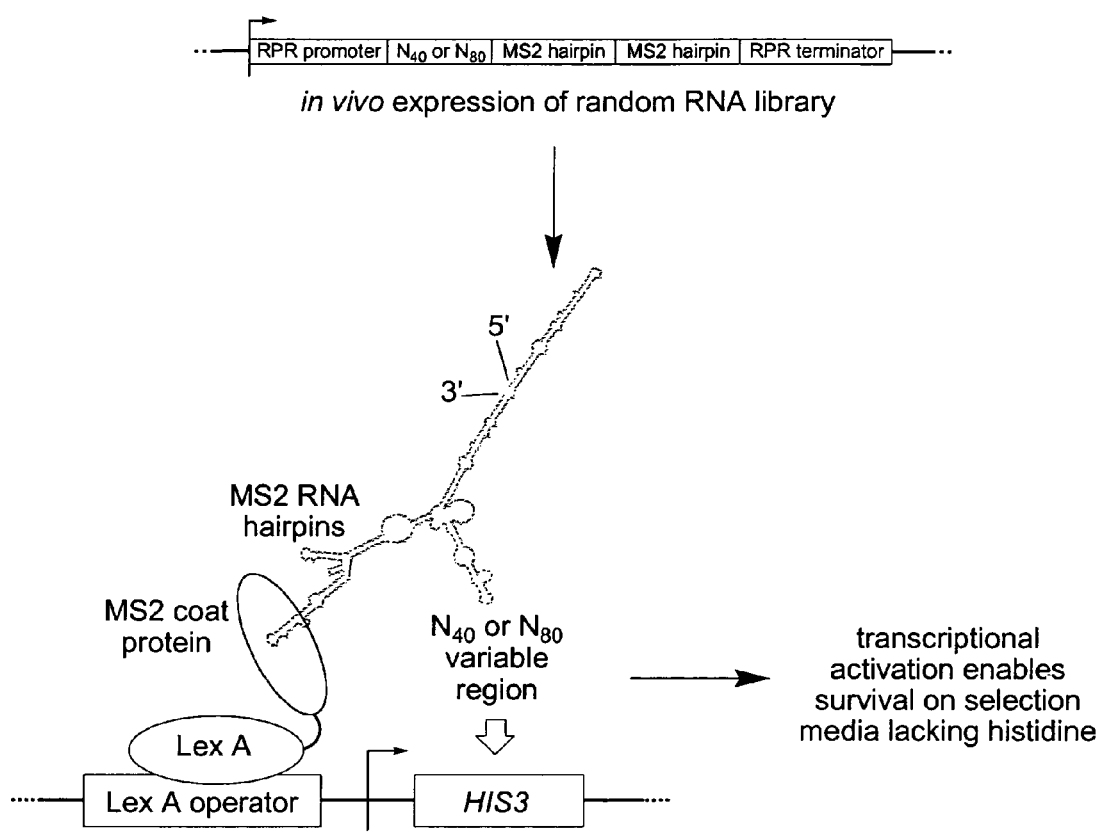
FIG. 1 shows the library and selection design. RNA libraries containing a 5' leader sequence, a random $N_{40}$ or $N_{80}$ region, two MS2 hairpins, and a terminator were expressed in yeast and localized to the promoter region of a HIS3 gene by binding to a MS2 RNA-binding protein fused to the DNA binding protein LexA (Bernstein, D. S., Buter, N., Stumpf, C., and Wickens, M. (2002). Analyzing mRNA-protein complexes using a yeast three-hybrid system. Methods 26, 123-141). RNA library members that activate transcription of HIS3 allow survival on selection media lacking histidine.

A system for regulating transcription using RNA-based transcriptional regulators is described herein. These RNA-based transcriptional regulators, which can inhibit or promote the transcription of a gene of interest, are designed or evolved based on the idea that RNA can adopt a 3-D structure that mimics the activation domain of protein transcriptional activators. The RNA-based transcriptional regulators of the invention are useful in both research and clinical settings. They may be used in the lab to probe biological pathways, development, biochemical interactions, and cell biology. In the clinic, they may be used to prevent and treat diseases such as cancer, genetic diseases, autoimmune diseases, cardiovascular disease, and inflammation. Given the importance of transcription in many biological processes, the regulation of transcription by RNA-based transcriptional regulators, especially those which can be controlled by the binding of a ligand, is a significant development in science and medicine.

RNA-Based Transcriptional Regulators

The RNA-based transcriptional regulators activate or suppress the transcription of a gene of interest. Without wishing to be bound by any particular theory, the regulators are thought to act by adopting a 3-D structure which mimics the structure of the activation domain of traditional protein transcriptional activators. The RNA-based regulators provide a surface which recruits the cellular machinery responsible for transcription to the gene of interest and/or induces a change in certain elements of the cellular machinery to promote or suppress transcription.

For the RNA-based transcriptional regulator to be effective in regulating transcription, it is typically recruited to the DNA template of the gene of interest. Preferably, the regulator is recruited to the promoter of the gene of interest, for example, within 2 kilobases of the promoter, preferably within 500 bases, more preferably within 100 bases of the promoter, and even more preferably within 50 bases of the promoter. In certain embodiments, the regulator is recruited to the DNA template through a DNA binding protein designed to bind an element of the RNA regulator. In other embodiments, the regulator is associated with a small molecule (e.g., bleomycin) or polynucleotide known to bind DNA. In certain embodiments, the regulator is covalently attached to a DNA binding protein, peptide, small molecule, polynucleotide, or other chemical compound. In yet other embodiments, the RNA regulator binds a protein which binds another protein that binds the DNA template thereby providing an indirect association with the DNA template. As will be appreciated by one of skill in this art, the RNA-based transcriptional regulator can be recruited to the DNA template by any direct or indirect method known in the art. In certain embodiments, the regulator is recruited to a specific gene, gene family, or operon. The specificity of regulation is typically imparted by the DNA binding protein, small molecule, biomolecule, or polynucleotide. In other embodiments, the regulator is recruited indiscriminately and/or nonspecifically to genes of the genome.

The RNA-based transcriptional regulators of the present invention include at least one region responsible for transcriptional regulation (i.e., activation or suppression). The regulator region of the RNA includes an RNA sequence ranging in size from 5 to 500 bases, more preferably from 10 to 100 bases, and even more preferably from 20 to 50 bases. The Examples below describe two sets of RNA sequences—40-mers and 80-mers—used in testing for transcriptional activation. The library of 40-mers were found to have a higher frequency of transcriptional activators than the library of 80-mers, indicating possibly that longer sequences do not adopt a conformation amenable to transcriptional regulation or that longer sequences are more susceptible to degradation in vivo. For example, longer RNA sequence may be too floppy, may not adopt a stable conformation, or may be more susceptible to degradation by cellular RNAses or hydrolysis. The nucleotides of the RNA sequence are preferably the As, Us, Gs, and Cs, which naturally make up RNA sequences, but the RNA sequence may include natural and unnatural bases, sugars, and linkages. In certain embodiments, RNA derivatives are used to stabilize and prevent degradation of the RNA-based transcriptional activator. For example, the use of unnatural bases may facilitate or prevent the intramolecular base pairing and facilitate the proper folding of the RNA. In another derivative, linkages such as phosphothioates provide a more stable linkage between nucleotides than the natural phosphodiester bond.

The RNA-based transcriptional activator may optionally contain other elements. These additional elements, which are preferably RNA-based, serve purposes other than regulating transcription. These other elements of the regulator may increase stability in vivo, increase conformational stability, lead to a particular folding, bind DNA, bind a protein such as a DNA-binding protein, bind an agent that binds DNA, or bind an agent responsible for activating or deactivating transcription. These other elements of the RNA-based transcriptional regulator may be RNA, DNA, proteins, peptides, polymers, or small molecules associated with the RNA sequence responsible for transcriptional regulation. In certain preferred embodiments, the other elements are RNA sequences covalently linked to the RNA sequence responsible for transcriptional regulation. This allows for the production of the RNA-based transcriptional regulator by the transcription of a complementary DNA sequence. In certain embodiments, the RNA sequences around the region responsible for transcriptional regulation are known to adopt a particular secondary structure (e.g., a hairpin loop, a stem loop). The secondary structure may increase the half-life of the RNA molecule in vivo. In certain embodiments, the secondary structure of the RNA allows it to bind a protein or other agent. The other regions are preferably used in recruiting the regulatory region to DNA. In certain embodiments, the RNA sequence includes a region which directly associates with DNA. In other embodiments, the RNA sequence is known to bind a protein which in turn binds DNA. In yet other embodiments, the RNA sequence (e.g., MS2 hairpin) is known to bind a fusion protein with a domain responsible for binding the RNA (e.g., MS2 coat protein) and another domain responsible for binding DNA (e.g., LexA). In yet another embodiment, the RNA sequence binds a protein known to interact with another DNA-binding protein.

Other regions/elements of the RNA-based transcriptional regulator may be used for isolation or characterization of the RNA sequence. For example, the RNA may contain primer binding sites for sequencing, reverse transcription, mutagenesis including site-directed mutagenesis, PCR amplification, or PCR mutagenesis. In other embodiments, the RNA may include tags (e.g., particular sequences) for purification. The RNA may also include sequences for cell processing such as transport or splicing.

Preferably the elements of an RNA-based transcriptional regulator are arranged so that the regulatory element(s) responsible for regulating transcription are presented on the outside of the folded RNA so that the regulatory element can recruit or exert its effect on the cellular transcription machinery necessary to initiate transcription. The regulatory element may also be placed between two elements of known stable conformations in order to protect it from degradation and/or stabilize the regulatory element in a particular conformation. The sequence of elements of the RNA-based transcriptional regulator will be determined by the functioning of each element and the setting in which the regulator will be used and how the regulator will be prepared and characterized. Preferably, the elements of the RNA-based transcriptional regulator are arranged so that the entire regulator adopts a stable conformation with intramolecular base pairing.

In certain embodiments of the claimed invention, the RNA-based transcriptional regulator contains one of the following sequences responsible for activating transcription:

```
                                                    (SEQ ID NO: 1)
N40-1      UUGUGAGCUGGCCUCCCGCGAUGGGGAUAACGCCACUGAA (SEQ ID NO: 2)
N40-4      CUGGUCCCGUCUCGCGGCGCCCUAGCGCAGUAAUUCUUCA (SEQ ID NO: 3)
N40-5      AUUUACAGCGCGGGCCGCUGUUUGUGUCUAGUGGCCUUGA (SEQ ID NO: 4)
N40-6      CGUCGCAAGCCGGUCUUGCGUCAUGGGCCUGAGGAAUUCG (SEQ ID NO: 5)
N40-7      ACGGCAUACCUGCUGGGGGGCGGGGCUGGCCCUCGUCGU (SEQ ID NO: 6)
N40-9      GGCGCCAAGCUGGUCUUAUGCGCUAGCUUGGGGGCCACC (SEQ ID NO: 7)
N40-11     GUAUUUCGCCCGGACGUGCGAUUGGUGGCUGGCCAUCAUU (SEQ ID NO: 8)
N40-13     GAUCGCAUAACAUGGGCGAUUGGUUCUGCUGGUCAGACCA (SEQ ID NO: 9)
N40-16     GAUUUAUGCCCCCUCCGGAGCUAUGCAUGAGCGGGCUCU (SEQ ID NO: 10)
N40-26     CGCGGAAGAAUGCUCCCCCAAGUGGAUGCCUAAGCCUCUU (SEQ ID NO: 11)
m5-9       GUUACAGCGCGGGCCGCUGUCUGUAUCUAUUGGCCGUGG (SEQ ID NO: 12)
m9-1       GGCGUCAAGCUGGUCUUAUGAGCUAGCUGGGGGGGCCACC
```

-continued

```
                                              (SEQ ID NO: 13)
m9-5       GGCGCCAAGCUGGUCUUAUGCGCUAGCGUGGGGUGGCCACC (SEQ ID NO: 14)
m9-6       AACGCCAAGCUGGUCUUAAGUGUCGCCUUGGGGAGCCACA (SEQ ID NO: 15)
m9-8       GGCGAAAAGCUGGUCUUGUGCUCUGGAAUGGUGGGCCACC (SEQ ID NO: 16)
m9-9       CGCCCUAAGCUGGUCUUAGGCGCCGGCUUGCGGGGCCACC (SEQ ID NO: 17)
m9-10      CGCGCCGAGCGGGUCUUGAGCGCAAGGAUGGACUACCGCC (SEQ ID NO: 18)
m9-11      GGGGCCGAGCCGGUCUCGUGCCCAAGCAAGGGGUGCCACCC (SEQ ID NO: 19)
m9-12      GGCGCCAGGCAGGUCCUGUGCGUUAGCCUGUGGGGCCACC (SEQ ID NO: 20)
m9-13      GGCGCGAAGCUGGUCUUUUGCGCCUGCUUAGGGAGCGACC (SEQ ID NO: 21)
m9-16      AGUGCCAAGCUGGCCUUAUGCACUACCUUCCGGCGCCACG (SEQ ID NO: 10)
N40-26     CGCGGAAGAAUGCU-CCCCCAAGUGGAUGCCUAAGCCUCUU (SEQ ID NO: 23)
m26-10     CGCGGAAGAAUGAU-CCCCCAAGUGGAUGCCUAAGCCUCUU (SEQ ID NO: 24)
m26-36     CGCGGAAGAAUUCU-CCCCCAAGUGGAUGCCUAAGCCUCUU (SEQ ID NO: 25)
m26-31     CGCGGAAGAAUGCU-CCCCCGAGUGGAUGCCUAAGCCUCAU (SEQ ID NO: 26)
m26-9      CGCGGAGGAAUGCU-CCCCCGAGUGGAUGCCUAAUCCUCUU (SEQ ID NO: 27)
m26-14     CGCGGAAGCAUACU-CCCCCGAGUGGAUGCCUAAGCCUCUU (SEQ ID NO: 28)
m26-15     CGCGGACCAAUGGU-CCCCCAAGUGGAUGCCUAAGCCUCUU (SEQ ID NO: 29)
m26-34     CGCGGAAGAUUGCC-CCCCCAAGUGGAUGCCUAAACCUCUA (SEQ ID NO: 30)
m26-29     CGCGGAAGAUUGUU-CCCCCAAGUGGAUGCCUAAACCUCAU (SEQ ID NO: 31)
m26-28     CGCGGAAAAAUACU-CCCCCAAGUGGAUGCCUAAACCUAUU (SEQ ID NO: 32)
m26-17     CGCGGAAGAAUGAU-CCCCCAGGUGGAUGCCUAAGCCUCUA (SEQ ID NO: 33)
m26-30     CGCGGAACAAUGCU-CCCCCAGCUGGAUGCCUAAGCCUCUA (SEQ ID NO: 34)
m26-20     CGGGGAAGAAUGCU-GCCCAAAGUGGAUGCCUAAGCCUCUU (SEQ ID NO: 35)
m26-4      CGCGGAAGAAUGCU-GCCCAACCUGGAUGCCUAAACCUCUU (SEQ ID NO: 36)
m26-32     CGCGGAAGAAUGCU-GCCCAACCUGGAUGCCUAAACCUCUU (SEQ ID NO: 37)
m26-13     CUCGGAACAAUGCC-CCCCCAAGUGGAUGCCUAAACCUCAU (SEQ ID NO: 38)
m26-35     CUCGGAAGAAUUCU-CCCGAUAGUGGAUGCCUAAGCCUCUU (SEQ ID NO: 39)
m26-16     CGCGGAAGAAGAGU-CCCCCGAGUGGAUGCCUAAACCUCUU (SEQ ID NO: 40)
m26-18     CGCGGAACAAUGUU-GCCCCAAAUGGAUGCCUAAGCCUCUU (SEQ ID NO: 41)
m26-25     CGCGGAAGAACACU-CCCCCACGUGGAUGCCUAAGCCUC-
           CUU (SEQ ID NO: 42)
m26-21     CGCGGAAGACUGCA-GCCCCAGGUGGAUGCCUAAAC-
           CUCGGU (SEQ ID NO: 43)
m26-39     CCCGGAAGACUGCA-GCCCCAGGUGGAUGCCUAAACCUCUU (SEQ ID NO: 44)
m26-33     CGCGGAAGACUUCA-GCCCCAAGUGGAUGCCUAAGCCU-
           CUUA (SEQ ID NO: 45)
m26-1      CGCGGGUGUAAGCC-CCCCCAGGUGGAUGCCUAAGCCUCUU (SEQ ID NO: 46)
m26-23     CGCGUAAACAUGCG-GCCCCAAGUGGAUGCCUAAGCCUCCU (SEQ ID NO: 47)
m26-24     CGCGGAAAGAUGAU-CACCCGAGUGGAUGCCUAAGCCUCUU (SEQ ID NO: 48)
m26-11     CGCGCGAGUAUACU-CCCCCAAGCGGAUGCCUAAGCCUCUU (SEQ ID NO: 49)
m26-19     CGCAGAAGAUACCU-CCCCCAAGUGGAUGCCUAAGCCUCAU (SEQ ID NO: 50)
m26-26     AACAGAAGAAUACU-CCCCCAAGUGGAUACCUAAGCAUCUU (SEQ ID NO: 51)
m26-37     CGCGGAAAAAUUCUUCCCCCAAGUGGAUGCCUAAGCCUCUU (SEQ ID NO: 52)
m26-38     CGCGGAAAAAUUCUUCCCCCAAGUGGAUGCGUAAGCCUCUU (SEQ ID NO: 53)
m26-7      CGCGGAAGAACGCU-CCCCGACGUGGAUGCCUAUUGUCCUU (SEQ ID NO: 54)
consensus  CGCGGAAGAAUGCU-CCCCCAAGUGGAUGCCUAAGCCUCUU
```

Particularly preferred sequences include N40-26, m26-11, and m26-12. The present invention also include various insertions, deletions, and point mutations in the above sequence. Other sequences of the invention include sequence that are at least 99%, 96%, 97%, 96%, 95%, 90%, 85%, 80%, 75%, and 50% homologous. In other embodiments, various portions of the above sequences may be mixed and matched to yield a sequence that activates transcription. As described in Example 1, the sequence is included in a RNA-based transcriptional regulator also containing two MS2 hairpins used to bind DNA through the MS2 coat protein/LexA fusion protein.

The RNA regulators of the present invention activate transcription at levels comparable to natural activators such as Gal 4 and VP16. In certain embodiments, the regulator activates 2-fold higher, 5-fold higher, 10-fold higher, 50-fold, higher, 100-fold higher, 1000-higher than a three-hybrid positive control using the Gal 4 activation domain. In other embodiments, the regulator activates at the same level, 10% less, 50% less, 75% less, 25% less, or 10% less than a three-hybrid positive control using the Gal 4 activation domain. The sequences evolved using the inventive system are typically much stronger activators than the RNA-based transcriptional activators previously disclosed in the literature. For many purposes, the greater the activation the more useful the RNA-based regulator is in clinical and experimental settings.

In certain preferred embodiments, the RNA-based transcriptional activators are ligand dependent. The RNA sequence responsible for transcriptional regulation bind an agent that causes the RNA to gain or lose the ability to regulate transcription. In certain embodiments, the binding of ligand leads to a 1.5 fold, 2 fold, 5 fold, 10 fold, 20 fold, 50 fold, 100 fold, 1000 fold increase or decrease in the regulator's ability to regulate transcription. Work by Breaker and co-workers has shown that RNA "riboswitches" can be prepared that modulate translation. The modular nature of RNA aptamers that bind agents such as small molecules makes them particularly useful in designing ligand-dependent RNA-based transcriptional regulators. Without wishing to be bound by any particular theory, the binding of an agent such as a small molecule causes a conformational change in the RNA thereby modulating the RNA's ability to regulate transcription. Preferably, the effect of ligand binding is dose-dependent (e.g., as the concentration of ligand increases the ability of the regulator to affect transcription increases). Agents useful in regulating the RNA activator's ability to regulate transcription include any chemical compound. Examples of agents include small molecules (e.g., theophylline, TPP, neomycin, tetramethylrosamine (TMR), ethidium bromide, bleomycin), peptides, natural and unnatural amino acids (e.g., tryptophan, phenylalanine, tyrosine, lysine), proteins, polynucleotides, metals and metal ions (Mg, Mn, Zn, Co. Fe), organometallic complexes, metabolites, and polymers. In certain preferred embodiments, small molecules are the agents used. Preferably, an RNA aptamer is known which binds the agent; therefore, RNA binding or intercalating small molecules are particularly useful in this embodiment of the present invention. In certain other embodiments, the agent is an aromatic intercalator. Preferably, the RNA has a high affinity for the agent, for example, preferably less than 10 µM, less than 1 µM, less than 100 nM, or less than 10 nM. In certain embodiments, a ligand-binding RNA aptamer is designed or evolved separately (see WO 92/14843; WO 92/05285; U.S. Pat. No. 6,706,481; each of which is incorporated herein by reference) and then incorporated into a RNA-based transcriptional regulator.

Figure 6:
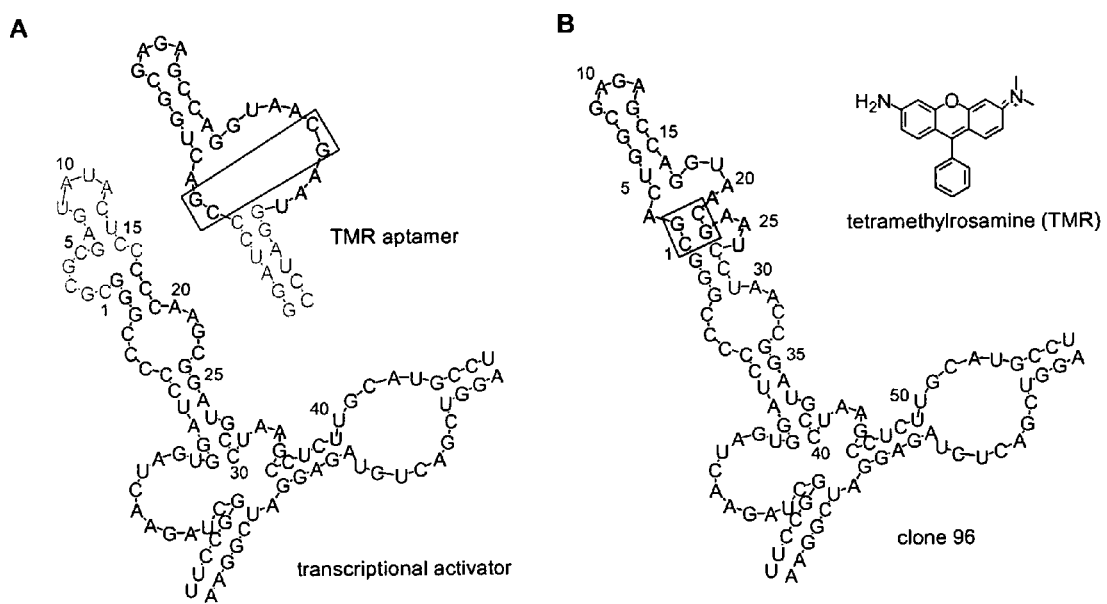
FIG. 6 shows the design of a ligand-dependent transcriptional activator (SEQ ID NO: 104, SEQ ID NO: 105 AND SEQ ID NO: 106).

Based on structural studies (including computer modeling) of the RNA regulator and the ligand-binding RNA aptamer, one of skill in the art designs the ligand-dependent RNA transcriptional activator by inserting the sequence of the aptamer into the RNA transcriptional activator based on factors including destabilizing and stabilizing effects of ligand binding, important bases for transcriptional regulation, secondary structure of both aptamer and RNA-based transcriptional regulator, bases pairing of RNA sequence, nature of ligand, etc. After the initial activator is prepared or several initial designs are prepared, the sequence may be evolved as described below to increase the specificity or ligand-dependence of the RNA-based transcriptional activator. In one embodiment described in Example 2 below, an aptamer known to bind tetramethylrosamine (TMR) was used to create an TMR-dependent RNA-based transcriptional activator (see FIG. 6). Based on structural models, it was hypothesized that when bases 1-16 of m26-11 were replaced with the core of the TMR-binding aptamer, the resulting flexibility of the loop without TMR bound would render the RNA inactive with respect to activating transcription. However, upon the addition of TMR, the TMR would bind the aptamer stabilizing the C:G base pairs thereby rendering the RNA active again (see FIG. 6).

The RNA-based transcriptional regulators of the present invention may be prepared using any methods known in the art for preparing RNA. These techniques include automated synthesis of RNA, isolation from a cell, and in vitro transcription of a complementary DNA template (see, e.g., Sambrook et al. *Molecular Cloning: A Laboratory Manual,* 2nd Ed., 1989; Ausubel et al., eds., *Current Protocols in Molecular Biology,* 1987; each of which is incorporated herein by reference). In certain embodiments, the RNA may be modified to increase its stability (e.g., methylation, alkylation, modified bases may be used, or an alternative to the phosphodiester bond may be used to link the nucleotides together). In certain embodiments, once the RNA is designed, the complementary DNA is prepared with the necessary promoter (e.g., RPR promoter) and terminator (e.g., RPR terminator) to have the DNA transcribed into RNA in a living cell or in an in vitro transcription system. Vectors (e.g., plasmids) engineered to produce the RNA-based transcriptional regulators are an aspect of the present invention. Using a vector, the desired RNA is produced in vivo and isolated using techniques known in the art. Techniques for purifying RNA include precipitation and column chromatography. In isolating RNA, careful attention must be paid to avoid contamination of any RNA-containing solution or suspension with RNA-degrading enzymes. In purifying RNA from a cell lysate, the RNA-degrading enzymes are preferably inhibited or inactivated as early in the purification process as possible to avoid degradation of the desired RNA.

Evolution of RNA-Based Transcriptional Activators

The present invention provides a process for evolving RNA-based transcriptional regulators. In certain embodiments, the regulators are evolved to increase the ability of the regulator to promote transcription. In other embodiments, a ligand-dependent transcriptional activator is evolved to increase its dependence on the ligand and/or increase its ability to regulate transcription. The evolution process involves providing at least one RNA sequence to be evolved, mutating that sequence to generate a collection of mutated sequences, and selecting the sequences with the desired activity. The steps of the process may be optionally repeated for the selected sequences to further evolve the RNA-based transcriptional regulator.

At least one RNA sequence is needed to begin the evolution process; however, in most embodiments a collection of RNA sequences will be used in the evolution process. The collection may contain up to 10, up to 50, up to 100, or up to 200 sequences for evolution. As will be appreciated by one of skill in this art, the number of sequences in the collection will typically be larger for RNA sequences that are longer. Also, a larger pool of starting sequences can substantially shorten the number of iterations necessary to reach a desired activity level. Typically, the RNA sequence(s) to be evolved will be contained within a vector so that it can be easily amplified, sequenced, mutated, and selected for. Typically the first library of sequences is produced by DNA synthesis using an automated DNA synthesizer. The DNAs are then ligated into a plasmid or other vector using techniques known in the art. The resulting vector can then be used to transform cells for the selection process. Cells useful in the selection process include any experimental cell line including bacteria such as *E. coli,* yeast such as *S. cerevisiae,* CHO cells, human cell lines, etc. The cells useful in the selection process may have been genetically altered, for example, the genes in the biosynthesis of an essential nutrient may have been mutated making the cells dependent on an external source of the nutrient or a plasmid including a wild type version of the mutated gene.

After the library of sequences has been obtained, the library can be mutated before selection to increase the diversity in the library, or it can be used to select for the desired activity without the mutation step. The plasmids are transformed into a cell line, bacteria, or yeast, as described above, and the transformed cells are grown under conditions such that only the clones producing RNA-based transcriptional regulators will survive and grow. For example, the plasmids may be transformed into a yeast strain which cannot synthesize an essential nutrient (e.g., an amino acid, uracil, adenine). The transformed yeast are then grown on media lacking this essential nutrient. Only the clones producing an RNA-based transcriptional regulator that turns on the missing enzyme in the biosynthesis of the essential nutrient will survive. The stringency of the screening may optionally be increased by adding an inhibitor of the enzyme (e.g., 3-aminotriazole is a competitive inhibitor of HIS3) to the growth media. After selection, the clones found able to grow may be further characterized by sequencing of the DNA sequence encoding the RNA-based transcriptional activator.

If greater activity is desired, the selected sequences can be mutated by any method known in the art and re-selected for clones with even greater activity. In certain embodiments, the mutated sequences are prepared by synthesis on a DNA synthesizer. In other embodiments, the mutations are introduced by error-prone PCR. The rate of mutation may be less than 5%, less than 10%, less than 20%, or less than 30%. The second generation library of sequences is transformed into cells and selected as described above for the first generation library of sequences. The method can be repeated multiple time (2×, 3×, 5×, 10×) to generate RNA-based transcriptional regulators with the desired activity.

The reagents, vectors, cell lines, and instructions may be provided in a kit for experimental convenience. The user of the kit may supply the DNAs encoding the RNA-based transcriptional regulators or an initial library of DNAs may be provided in the kit. The kit may contain reagents for a one time use or may contain enough of each reagent for multiple uses/rounds of selection.

Uses of RNA-Based Transcriptional Regulators

The RNA-based transcriptional regulators find use in both the experimental and clinical setting. Many biological process both physiological and pathological depend on the regulation of transcription of a gene. Some of these process include cell division, development, cell growth, signaling, response to cell stimuli, adaptation, etc. The RNA-based transcriptional regulators are used to alter the expression of a gene in a cell by transfecting the cell with a vector containing the DNA encoding the regulator. Transcription of the DNA encoding the regulator allows for the regulation of a gene in the cell allowing one to study the effect of increasing or decreasing the transcription of a gene. The method of using RNA-based transcriptional activators is made more useful by employing ligand-dependent RNA-based transcriptional activators. In this way, the transcription of a gene can be regulated by the addition of a ligand to cell transformed with a DNA encoding the RNA-based transcriptional regulator.

Any type of cell may used in the inventive method. For example, the cell may be of bacterial, fungal, plant, or animal origin. In certain preferred embodiments, the cells are *E. coli*. In other preferred embodiments, the cells are yeast cells. In yet other embodiments, the cells are mammalian cells such as experimental cell line (e.g., CHO cell lines, COS cells, Jurkat cells, etc.). The cells are preferably genetically altered to express a DNA binding protein that will recruit the RNA-based transcriptional regulator to the gene of interest. For example, the cell may express a LexA-MS2 coat protein fusion as described in the Examples below. In certain embodiments, the expression of a particular gene or family of gene is regulated.

The RNA-based transcriptional regulators of the invention are also useful in the prevention and treatment of diseases. Many diseases process involve the transcription of a gene including cancer, benign neoplasms, inflammation, autoimmune diseases, cardiovascular diseases, diabetic retinopathy, and infectious diseases. By inhibiting the transcription of a gene that is being overly transcribed using an RNA-based transcriptional activator, one can prevent, lessen, or cure the disease. The DNA vector encoding the RNA-based transcriptional activator is administered using any method known in the art. Preferably the DNA vector as a pharmaceutical composition is delivered using methods known in the gene therapy field. For example, the DNA vector may be delivered in a liposome. In another embodiments, cells are removed from the subject's body, transfected with the DNA vector encoding the RNA-based transcriptional activator, and then reintroduced into the subject's body. Cells such as bone marrow cells and stem cell are particularly useful in this embodiment of the invention.

The RNA-based transcriptional regulators, vectors encoding the RNA-based transcriptional regulators, and the methods of regulating gene expression via RNA-based transcriptional regulators are useful in probing biological pathways as well as useful in treating diseases resulting from errors in gene expression.

This and other aspects of the present invention will be further appreciated upon consideration of the following Examples, which are intended to illustrate certain particular embodiments of the invention but are not intended to limit its scope, as defined by the claims.

EXAMPLES

Example 1

In Vivo Evolution of an RNA-Based Transcriptional Activator

Introduction

In addition to its role as a transient carrier of genetic information within a cell, RNA is now known to play a functional role in several biological processes including tRNA processing, intron splicing, and peptide-bond formation during translation (Doudna, J. A., and Cech, T. R. (2002). The chemical repertoire of natural ribozymes. Nature 418, 222-228; Moore, P. B., and Steitz, T. A. (2002). The involvement of RNA in ribosome function. Nature 418, 229-235). The recent discovery of a class of small RNAs that block translation by base pairing to the 3' untranslated region of mRNAs reveals that natural RNAs can also regulate gene expression (Lau, N. C., Lim, L. P., Weinstein, E. G., and Bartel, D. P. (2001). An abundant class of tiny RNAs with probable regulatory roles in *Caenorhabditis elegans*. Science 294, 858-862). O'Malley and co-workers recently discovered an RNA that plays a structural role in a protein-RNA complex that co-activates genes regulated by steroid hormone receptors (Lanz, R. B., McKenna, N. J., Onate, S. A., Albrecht, U., Wong, J., Tsai, S. Y., Tsai, M. J., and O'Malley, B. W. (1999). A steroid receptor coactivator, SRA, functions as an RNA and is present in an SRC-1 complex. Cell 97, 17-27; Lanz, R. B., Razani, B., Goldberg, A. D., and O'Malley, B. W. (2002). Distinct RNA motifs are important for coactivation of steroid hormone receptors by steroid receptor RNA activator (SRA). Proc Natl Acad Sci USA 99, 16081-16086). An RNA that functions as a transcriptional activation domain, however, has not yet been discovered in nature.

The repertoire of natural functional roles played by RNA suggests that a directed evolution approach might enable the discovery of artificial RNA sequences that perturb cellular functions. These intracellularly expressed RNAs may serve as useful probes of complex biological systems and as tools for identifying targets involved in cellular processes of interest. Three recent reports describing random peptide libraries coupled with phenotypic selection (Norman, T. C., Smith, D. L., Sorger, P. K., Drees, B. L., O'Rourke, S. M., Hughes, T. R., Roberts, C. J., Friend, S. H., Fields, S., and Murray, A. W. (1999). Genetic selection of peptide inhibitors of biological pathways. Science 285, 591-595; Geyer, C. R., Colman-Lerner, A., and Brent, R. (1999). "Mutagenesis" by peptide aptamers identifies genetic network members and pathway connections. Proc Natl Acad Sci USA 96, 8567-8572; Blum, J. H., Dove, S. L., Hochschild, A., and Mekalanos, J. J. (2000). Isolation of peptide aptamers that inhibit intracellular processes. Proc Natl Acad Sci USA 97, 2241-2246) have shown that peptide aptamers ("peptamers") within natural protein scaffolds can be used in a forward genetics manner to probe the function and mechanism of biological pathways. Although a small number of studies involving the evolution of functional RNAs from random sequence libraries in vivo have been reported (Ferber, M. J., and Maher, L. J., 3rd (1998). Combinatorial selection of a small RNA that induces amplification of IncFII plasmids in *Escherichia coli*. J Mol Biol 279, 565-576; Soukup, G. A., and Maher, J. J., 3rd (1998). Selection and characterization of RNAs that relieve transcriptional interference in *Escherichia coli*. Nucleic Acids Res 26, 2715-2722; Zimmerman, J. M., and Maher, L. J., 3rd (2002). In vivo selection of spectinomycin-binding RNAs. Nucleic Acids Res 30, 5425-5435), random RNA libraries have not to our knowledge been evolved in vivo to study natural cellular function.

We envision RNA as offering potential advantages over peptamers in experiments of this type. While the chemical functionality of RNA may be less diverse than that of peptides, a larger fraction of a random RNA pool may form stable secondary structures (through base pairing) compared with the fraction of similarly sized random peptides that can form well-folded motifs (Keefe, A. D., and Szostak, J. W. (2001). Functional proteins from a random-sequence library. Nature 410, 715-718). This ability may give random RNAs greater structural variation than is available to random peptides inserted into an exposed loop constrained by a stable protein scaffold. In addition, basic structure-function relationships within RNA aptamers can often be revealed using site-directed mutagenesis and covariance analysis coupled with secondary structure prediction, while analogous experiments on peptide sequences can be much more difficult. Finally, researchers have established general methods for rationally engineering RNA that enable its function to be modulated using antisense oligonucleotides or using ligand-binding aptamers. These efforts have successfully generated sequence-regulated or allosteric functional RNAs (Soukup, G. A., and Breaker, R. R. (2000). Allosteric nucleic acid catalysts. Curr Opin Struct Biol 10, 318-325), while analogous efforts to engineer conditionally active peptide aptamers have not been reported.

The complexity of eukaryotic transcriptional activation makes this process an ideal candidate for validating our approach to perturbing cellular function with evolved RNAs. We report here the evolution of RNA-based activation domains and their characterization using site-directed mutagenesis and secondary structure prediction. The most potent evolved RNAs activate transcription to a degree comparable to that of the strongest known natural protein activation domains. Our findings demonstrate the use of RNA evolution in vivo to perturb complex biological pathways and provide a basis for engineering sequence-specific or ligand-modulated RNA-based transcription factors.

Results

Transcriptional Activation Selection

Eukaryotic transcription factors typically consist of two modular protein domains: a DNA-binding domain and an activation (or repression) domain. The recruitment model of Ptashne and Gann (Ptashne, M., and Gann, A. (1997). Transcriptional activation by recruitment. Nature 386, 569-577) suggests that the primary function of the activation domain is to make specific interactions with the RNA polymerase II holoenzyme that localize the proteins responsible for transcriptional initiation to a given promoter. This model does not require that recruitment occur through protein-protein interactions and we hypothesized that RNA-based transcriptional activators could be evolved in vivo if an RNA library was localized to the promoter of a selectable genetic marker. This approach requires three components: a yeast strain containing a selectable reporter gene, a method for tethering RNA to this reporter gene, and a vector that expresses a random library of stable RNAs. We used the yeast three-hybrid strain YBZ-1 developed by Wickens and co-workers (Bernstein, D. S., Buter, N., Stumpf, C., and Wickens, M. (2002). Analyzing mRNA-protein complexes using a yeast three-hybrid system. Methods 26, 123-141) to provide the first two components. The expression of both a HIS3 gene and a lacZ gene in YBZ-1 is driven by promoters that contain upstream LexA binding sites. The strain also expresses a LexA-MS2 fusion protein that binds both to these operator sites and also to the 19-base pair MS2 RNA hairpin with extremely high affinity ($K_d=2\times 10^{-10}$ M (Bernstein, D. S., Buter, N., Stumpf, C., and Wickens, M. (2002). Analyzing mRNA-protein complexes using a yeast three-hybrid system. Methods 26, 123-141)). RNAs containing an MS2 hairpin are therefore localized to the promoter of the HIS3 and lacZ genes (FIG. 1). Because expression of HIS3 or LacZ can be selected or quantitated, respectively, Wickens, Fields, and co-workers used this system to discover cellular RNA targets of an RNA-binding protein that was fused to a known protein transcriptional activator (SenGupta, D. J., Wickens, M., and Fields, S. (1999). Identification of RNAs that bind to a specific protein using the yeast three-hybrid system. RNA 5, 596-601). Encouragingly, sequences not requiring any RNA-binding protein were also noted (SenGupta, D. J., Wickens, M., and Fields, S. (1999). Identification of RNAs that bind to a specific protein using the yeast three-hybrid system. RNA 5, 596-601), suggesting that certain genome-encoded RNAs might be able to activate transcription without a protein transcriptional activator.

Expression and Selection of RNA Libraries

The stability of a random RNA library in vivo is a major challenge because unstructured RNAs can be rapidly degraded in the cell. To maximize the stability of our RNA libraries, we designed the variable region to lie within a larger RNA having known stable secondary structures at its 5' and 3' termini. In the pIII-MS2 vector constructed by Wickens and co-workers (Zhang, B., Kraemer, B., SenGupta, D., Fields, S., and Wickens, M. (2000). Yeast three-hybrid system to detect and analyze RNA-protein interactions. Methods Enzymol 318, 399-419), RNA library members are transcribed by RNA polymerase III from the RNase P RNA gene (RPR) promoter (Good, P. D., and Engelke, D. R. (1994). Yeast expression vectors using RNA polymerase III promoters. Gene 151, 209-214) and are not modified or translated (Bernstein, D. S., Buter, N., Stumpf, C., and Wickens, M. (2002).

Analyzing mRNA-protein complexes using a yeast three-hybrid system. Methods 26, 123-141). We inserted a random 40-base region ($N_{40}$) or 80-base region ($N_{80}$) into the transcribed region followed by two MS2 hairpins. The transcript ends with the RPR terminator to enhance stability of the 3' end of the RNA library (FIG. 1).

Prepared pIII-MS2 backbone DNA was ligated with a synthetic DNA cassette encoding the $N_{40}$ or $N_{80}$ library, amplified in *E. coli* (initial diversity of $1.1 \times 10^7$ *E. coli* transformants for each library), and transformed into YBZ-1 yielding $10^4$-$10^5$ transformants. The yeast libraries were plated on media lacking histidine to select for HIS3 transcriptional activation and expression. Initial survivors were each screened by plating on fresh media lacking histidine. Red colonies (which presumably lost the pIII-MS2 plasmid containing ADE2) and clones that failed to grow again were discarded. For the $N_{40}$ library, clones passing the initial selection and screening were observed at a surprisingly high frequency of 0.2%. In contrast, the $N_{80}$ library yielded a lower frequency of positives (0.01%). These results suggest that a significant fraction of our random RNA libraries are able to activate transcription when localized to a promoter.

Characterization of Initial Selected RNAs

Figure 2:
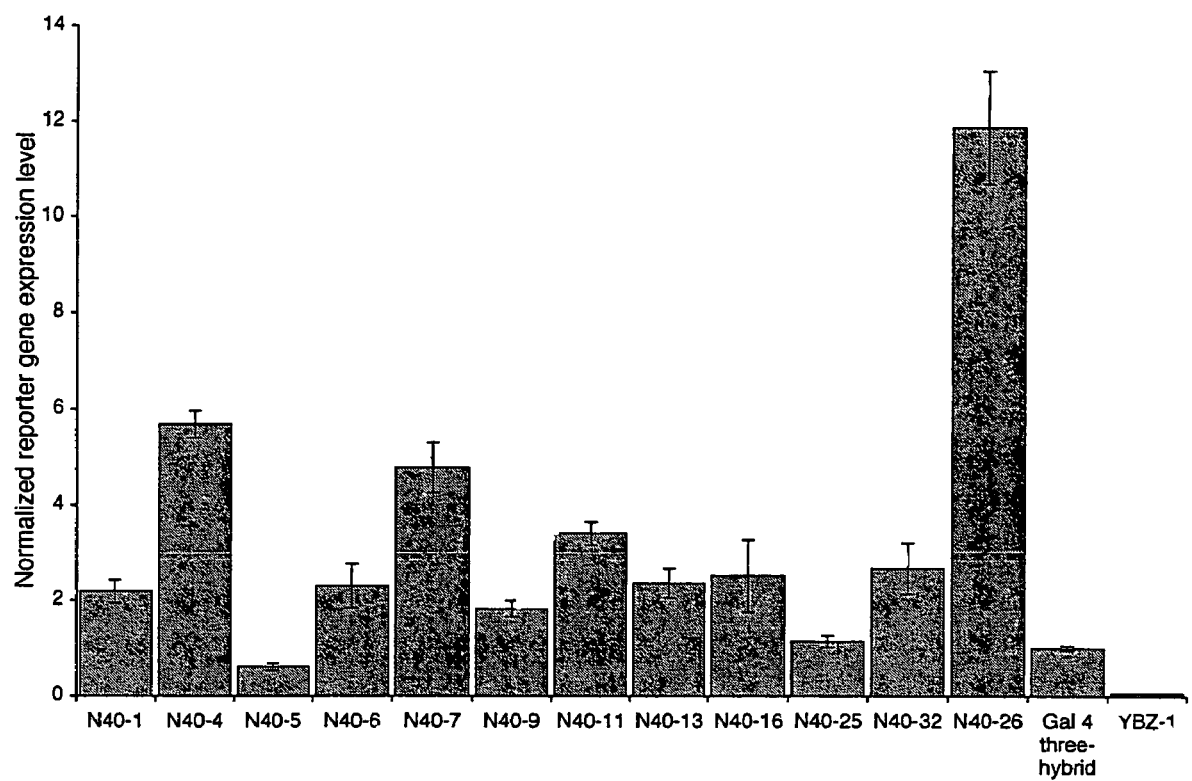
FIG. 2 depicts the transcriptional activation abilities of original selected RNAs. Quantitative β-galactosidase assays (Pryciak, P. M., and Hartwell, L. H. (1996). AKR1 encodes a candidate effector of the G beta gamma complex in the *Saccharomyces cerevisiae* pheromone response pathway and contributes to control of both cell shape and signal transduction. Mol Cell Biol 16, 2614-2626) of cell lysates from the eleven most potent $N_{40}$ activators were performed at least three times each from independently grown clones. The average activity per clone is shown normalized relative to the Gal4 three-hybrid positive control (=1.0). Error bars reflect standard deviations.

We characterized 70 total survivors from both libraries by retransformation into fresh YBZ-1 cells and quantitation of β-galactosidase expression levels from cell extracts. As a positive control, we used the known three-hybrid interaction between MS2 hairpin-IRE RNA and the IRP-Gal4 fusion protein, which leads to recruitment of the strongly activating Gal4 domain to the LexA operator and activation of the reporter genes (SenGupta, D. J., Zhang, B., Kraemer, B., Pochart, P., Fields, S., and Wickens, M. (1996). A three-hybrid system to detect RNA-protein interactions in vivo. Proc Natl Acad Sci USA 93, 8496-8501). Results from β-galactosidase expression assays are shown in FIG. 2 for the 11 strongest selected members of the $N_{40}$ library. All eleven activate LacZ expression at least as strongly as the Gal4 positive control. One clone (N40-26) activated LacZ expression more than ten times as strongly as the Gal 4 positive control (FIG. 2). Because the library was selected on the basis of HIS3 transcriptional activation yet characterized by activation of LacZ expression, these results indicate that survivors encode general, rather than gene-specific, RNA-based transcriptional activators. From the $N_{80}$ library only three clones of the 46 assayed demonstrated LacZ expression levels comparable to that of the positive control and were not further characterized.

The secondary structures of the 11 most active clones from the $N_{40}$ library were predicted using the mfold method (Mathews, D. H., Sabina, J., Zuker, M., and Turner, D. H. (1999). Expanded sequence dependence of thermodynamic parameters improves prediction of RNA secondary structure. J Mol Biol 288, 911-940). While the MS2 hairpins and 5' leader sequence in the constant region maintained the same predicted secondary structure among the active clones, both the variable regions as well as the constant regions near their junction were predicted to adopt a wide variety of different structures (not shown). These results suggest that transcriptional activator RNAs may operate through a variety of different mechanisms and possibly a variety of different targets, or that several different RNA structures can form interactions with the same target leading to transcriptional activation.

Evolution of More Potent Activators

To determine if these initial clones could be further evolved towards stronger transcriptional activation, we increased the stringency of the selection for HIS3 expression by adding 3-aminotriazole (3-AT), a competitive inhibitor of His3 activity, to the growth media (Zhang, B., Kraemer, B., SenGupta, D., Fields, S., and Wickens, M. (2000). Yeast three-hybrid system to detect and analyze RNA-protein interactions. Methods Enzymol 318, 399-419). Freshly transformed YBZ-1 yeast expressing N40-26 can grow on selection media containing 1 mM 3-AT, while freshly transformed yeast that express RNAs with activities below that of the positive control fail to grow in the presence of 1 mM 3-AT. These results indicate that 3-AT can be used to increase the dynamic range of the selection and therefore can enable more potent transcriptional activator RNAs to be distinguished from less active sequences.

Figure 3:
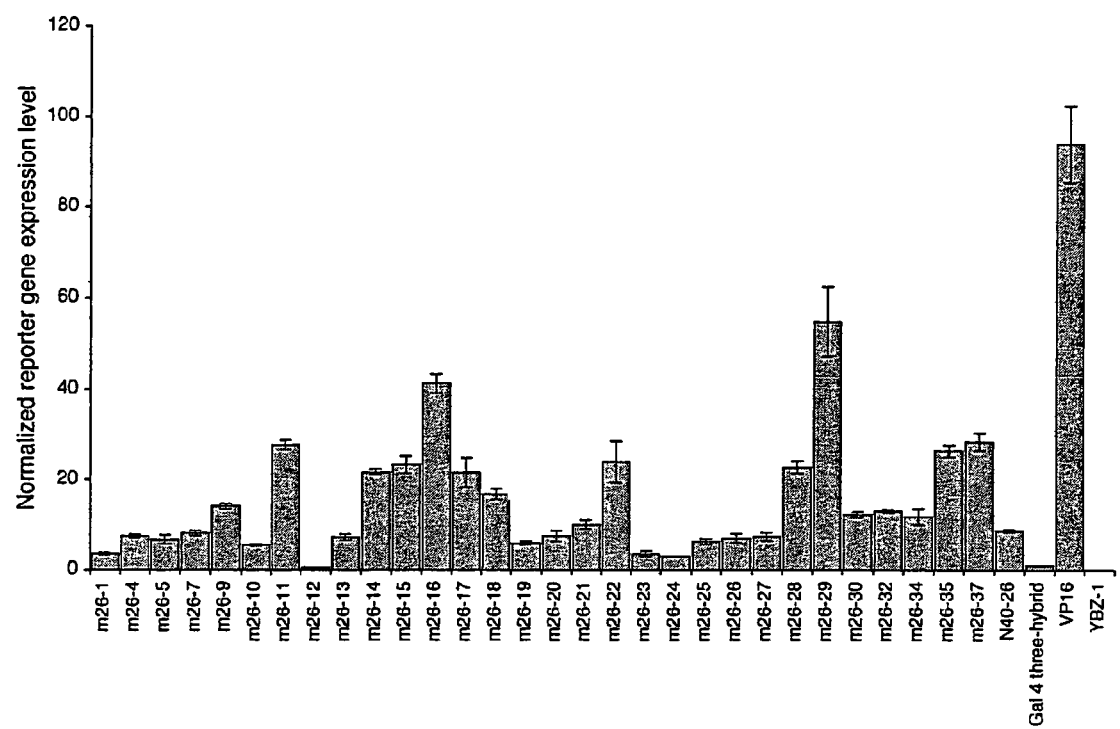
FIG. 3 demonstrates the transcriptional activation abilities of evolved N40-26 variants. Quantitative β-galactosidase assays (Pryciak, P. M., and Hartwell, L. H. (1996). AKR1 encodes a candidate effector of the G beta gamma complex in the *Saccharomyces cerevisiae* pheromone response pathway and contributes to control of both cell shape and signal transduction. Mol Cell Biol 16, 2614-2626) of cell lysates from 30 evolved N40-26 mutants were performed at least three times each from independently grown clones. The average activity per clone is shown normalized relative to the Gal4 three-hybrid positive control (=1.0). Error bars reflect standard deviations.

We generated a library of variants of our strongest initially selected RNA activator, N40-26, in which each of the 40 bases in the variable region was randomly mutated at a frequency of 20%. DNA sequencing of 14 library members before selection revealed an average of 9.0 mutations per clone, close to the anticipated value. High stringency selection of this library ($1.4 \times 10^5$ yeast transformants from an original diversity of $5.5 \times 10^7$ *E. coli* transformants) in the presence of 1 mM 3-AT yielded 40 survivors containing 32 unique sequences. Each of the 32 evolved clones was characterized by retransformation and β-galactosidase assay (FIG. 3). Fifteen of the clones possessed a transcriptional activation activity higher than that of the starting clone N40-26. Only one clone (m26-12) was much less active than the parental N40-26 RNA. The most active evolved clone, m26-29, activates transcription of the reporter gene more than 5-fold stronger than N40-26, and 53-fold stronger than the Gal4 activation domain positive control.

To compare the m26-29 RNA with one of the most potent and well-characterized natural protein transcriptional activators known, we expressed a LexA-VP16 fusion protein from the ADH promoter on a single copy vector in L40-ura3 to mimic the expression levels of the LexA-MS2 fusion protein. Remarkably, the m26-29 RNA activated gene expression only 2-fold lower than that of VP16 fused directly to LexA (FIG. 3), even though the RNA-based activator requires an additional interaction (between the MS2 hairpin and the MS2 binding protein domain) that may decrease the efficiency of transcriptional activation. Ptashne and co-workers (Sadowski, I., Ma, J., Triezenberg, S., and Ptashne, M. (1988). GAL4-VP16 is an unusually potent transcriptional activator. Nature 335, 563-564) previously compared the transcriptional activation of intact Gal4 with Gal4-VP16 fusions and found that VP16 activates transcription 100-fold more potently than Gal4; this ratio is consistent with our observation that m26-29 RNA activates transcription 53-fold higher than the three-hybrid Gal4 control and 2-fold lower than VP16. Taken together, these results indicate that the mutagenesis and high stringency selection strategy applied to N40-26 resulted in the evolution of significantly improved RNAs that rival the effectiveness of the most potent known transcriptional activator proteins.

Characterization of Evolved Activators

To test whether the evolved RNAs require the MS2 protein-mediated localization to the LexA promoter, we introduced the plasmids expressing two representative active clones (m26-11 and m26-15) into the yeast strain L40-ura3 which lacks the LexA-MS2 fusion protein but is otherwise identical to YBZ-1 (Bernstein, D. S., Buter, N., Stumpf, C., and Wickens, M. (2002). Analyzing mRNA-protein complexes using a yeast three-hybrid system. Methods 26, 123-141). As expected, the resulting cells were unable to survive on media lacking histidine, indicating that localization of the evolved RNAs to the reporter gene is required for transcription activation.

An alignment of the sequences of 32 evolved N40-26 variants is shown in FIG. 4. All evolved N40-26 variants were closely related with the sole exception of the much less active m26-12 clone (not shown). Surprisingly, the consensus sequence is the same as the N40-26, suggesting that N40-26 is already somewhat optimized in its ability to activate transcription despite the significant improvements in activity upon mutagenesis and reselection. The 31 active sequences contained an average of 4.5 mutations each, indicating that only about 50% of the introduced mutations allowed RNAs to survive the higher stringency selection. These mutations were clustered at positions 4-15, 19-22, 34, and 39-40 within the 40-base variable region (FIG. 4).

Figure 5:
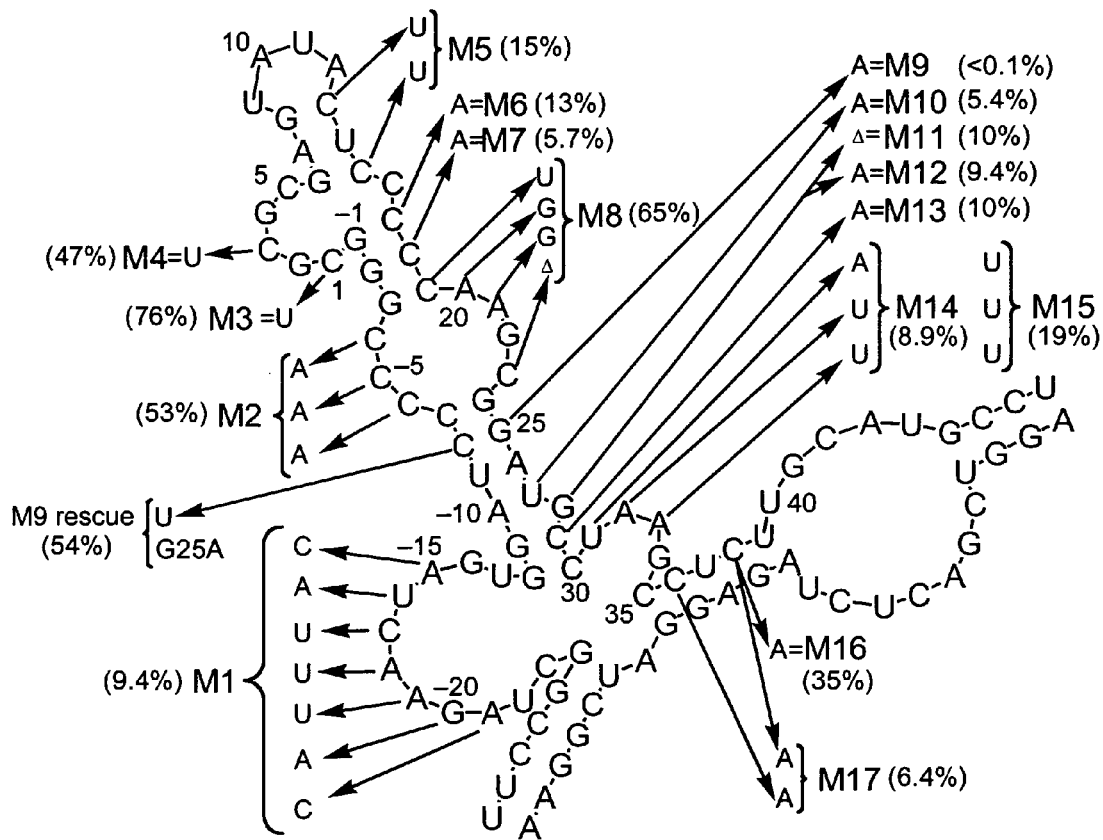
FIG. 5 shows the predicted secondary structure and strategy for site-directed mutagenesis of m26-11. Each set of single- or multiple-base mutations is labeled M1 through M17 to correspond with the data listed in Table 1. Highly conserved bases among N26-40 variants are shown in red. Activities of each mutation set are listed in parenthesis as a percentage relative to the activity of unmutated m26-11. Sequence m26-11 is SEQ ID NO: 104.

Three subsequences (bases 16-18, 23-33, and 35-38) are highly conserved among the evolved N40-26 variants (FIG. 4). Interestingly, these conserved subsequences correspond to three of the four regions of predicted secondary structure (Mathews, D. H., Sabina, J., Zuker, M., and Turner, D. H. (1999). Expanded sequence dependence of thermodynamic parameters improves prediction of RNA secondary structure. J Mol Biol 288, 911-940) (FIG. 5). Bases 17-18 (CC) are predicted to participate in pairing with the G-rich end of the 5' constant region; bases 24-30 may be involved in base pairing with the 5' constant region; and bases 35-38 may pair with four bases in the 3' terminator.

It is noteworthy that among the evolved sequences m26-12 uniquely lacks several of the conserved secondary structures and is also by far the weakest activator among the evolved N40-26 variants. In addition, the lack of predicted base pairing between conserved variable region bases (as opposed to between the variable and constant regions) among all of the evolved N40-26 variants is surprising and may suggest geometric constraints imposed by the structure of the constant region that disfavor base pairing within the variable region. In summary, the conserved subsequences emerging from random mutagenesis and reselection together with their predicted secondary structures collectively suggest several candidate structural elements that could play roles in transcriptional activation.

Structure-Activity Analysis of an Evolved RNA

An attractive feature of RNA aptamers is the possibility of using secondary structure prediction together with site-directed mutagenesis to infer and test structure-function relationships. We systematically installed a series of 16 single or multi-base site-directed mutations (Table 1 and FIG. 5) in the variable and constant regions of one of the most active evolved N40-26 variants, m26-11, and measured the ability of the resulting mutants to activate β-galactosidase transcription.

TABLE 1

Transcriptional activation abilities of site-directed mutants of m26-11 shown in FIG. 5. Quantitative β-galactosidase assays (Pryciak, P. M., and Hartwell, L. H. (1996). AKR1 encodes a candidate effector of the G beta gamma complex in the *Saccharomyces cerevisiae* pheromone response pathway and contributes to control of both cell shape and signal transduction. Mol Cell Biol 16, 2614-2626) of cell lysates were performed at three to nine times each from independently grown clones and average values are reported as the percentage of transcriptional activation relative to m26-11. Standard deviations are shown following each value.

| Mutation | Genotype | % Activity relative to m26-11 |
|---|---|---|
| M1 | A(−21)C<br>G(−20)A | 9.4 ± 1.3% |

TABLE 1-continued

Transcriptional activation abilities of site-directed mutants of m26-11 shown in FIG. 5. Quantitative β-galactosidase assays (Pryciak, P. M., and Hartwell, L. H. (1996). AKR1 encodes a candidate effector of the G beta gamma complex in the *Saccharomyces cerevisiae* pheromone response pathway and contributes to control of both cell shape and signal transduction. Mol Cell Biol 16, 2614-2626) of cell lysates were performed at three to nine times each from independently grown clones and average values are reported as the percentage of transcriptional activation relative to m26-11. Standard deviations are shown following each value.

| Mutation | Genotype | % Activity relative to m26-11 |
|---|---|---|
|  | A(−19)U<br>A(−18)U<br>C(−17)U<br>U(−16)A<br>A(−15)C |  |
| M2 | C(−6)A<br>C(−5)A<br>C(−4)A | 53 ± 2.7% |
| M3 | C1U | 76 ± 7.6% |
| M4 | C3U | 47 ± 4.7% |
| M5 | C13U<br>C15U | 15 ± 2.4% |
| M6 | C17A | 13 ± 2.0% |
| M7 | C18A | 5.7 ± 1.2% |
| M8 | C19U<br>A20G<br>A21G<br>ΔC23 | 65 ± 11% |
| M9 | G25A | <0.1% |
| M9rescue | C(−8)U<br>G25A | 54 ± 5.0% |
| M10 | U27A | 5.4 ± 0.15% |
| M11 | ΔG28 | 10 ± 1.4% |
| M12 | G28A | 9.4 ± 1.4% |
| M13 | C29A | 10 ± 2.0% |
| M14 | U31A<br>A32U<br>A33U | 8.9 ± 0.63% |
| M15 | A32U<br>A33U | 19 ± 1.1% |
| M16 | C38A | 35 ± 2.5% |
| M17 | C36A<br>C38A | 6.4 ± 0.5% |

We first perturbed nucleotides predicted to participate in base pairing within the three highly conserved regions described above. Variable region bases C17, C18, and C19 in m26-11 are predicted to pair with the GGG at the end of the 5' constant region (FIG. 5). Mutation of C17 to A (M6) or mutation of C18 to A (M7) reduces transcriptional activation by 8-fold and 17-fold, respectively (Table 1). The highly conserved GGAUGCC representing bases 24-30 is also predicted to pair with the 5' constant sequence. The G25A mutant (M9) possesses no measurable transcriptional activation activity (<0.1%). Similarly, a variety of mutations among the other bases predicted to form secondary structures in this region (M10, M11, M12, and M13), reduce activity by 10- to 20-fold (Table 1). The role of base pairing involving bases 35-39 was probed by the single mutation of C38 to A (M16), which resulted in a 3-fold reduction in transcriptional activation, as well as by a larger perturbation changing C36 and C38 to A36 and A38 (M17), which caused a 16-fold loss in activity. These results further highlight the importance of these three regions in transcriptional activation.

To test aspects of the predicted structural model within the largest conserved region (bases 23-33), we generated a secondary mutation designed to restore the activity of the least active m26-11 mutant (M9, G25A). The structural model in FIG. 5 predicts that base 25 of the variable region pairs with base −8 of the constant region. Replacing C(−8) with U, predicted to restore base pairing with the inactive G25A mutant, rescues transcriptional activation ability to 54% of the unmutated m26-11 (Table 1). The ability of a single compensating mutation at base −8 to restore the activity of an inactive point mutant provides strong support for the predicted secondary structure in this region. In addition, this result demonstrates that base pairing, but not base-specific contacts, at positions −8 and 25 are required for transcriptional activation.

Site-directed mutations outside of the three conserved regions predicted to participate in base pairing resulted in smaller losses in activity. Mutations M2, M3, M4, and M5 perturb constant and variable region bases upstream of the first conserved region and resulted in 1.3- to 7-fold decreases in activity. Indeed, bases 1-16 can even be replaced with an unrelated 26 base sequence without significant loss of transcriptional activation (data not shown). Mutation of the non-conserved bases 19-23 (M8) likewise resulted in less than 2-fold loss of activity. These findings suggest that mutations are more tolerated in regions predicted not to participate in base pairing. In support of this relationship between predicted base pairing and functional importance, mutating bases 31-33 (predicted to form an unpaired bulge between the two conserved putative stems) impaired activity by as little as 5-fold (M14 and M15), despite the highly conserved nature of these three nucleotides.

Discussion

We have described the in vivo selection of RNA sequences capable of activating transcription with potency comparable to the most active known protein transcriptional activation domains. Through a combination of further evolution, systematic site-directed mutagenesis, and secondary structure prediction, we elucidated structure-function relationships that identify regions of the evolved RNAs that play important functional roles. The potency of our evolved activators—up to 53-fold higher than a Gal4 three-hybrid positive control—is surprising given that the most active previously reported genomic RNA sequences with transcriptional activation properties (Sengupta, D. J., Wickens, M., and Fields, S. (1999). Identification of RNAs that bind to a specific protein using the yeast three-hybrid system. RNA 5, 596-601) are 5-fold less potent than the same Gal4 three-hybrid positive control (SenGupta, D. J., Zhang, B., Kraemer, B., Pochart, P., Fields, S., and Wickens, M. (1996). A three-hybrid system to detect RNA-protein interactions in vivo. Proc Natl Acad Sci USA 93, 8496-8501). Indeed, independent work by Ptashne and co-workers (Saha, S., Ansari, A., Jarell, K., and Ptashne, M. (2003). RNA sequences that work as transcriptional activating regions. Nucleic Acids Res 31, 1565-1570) used a similar selection (without additional rounds of mutagenesis and reselection) on a smaller, 10-base random region to isolate transcriptional activating RNAs that are 10-fold less potent than intact Gal4 and have no sequence homology to the RNAs described here. The significantly higher potency of the 40-base variable region RNAs evolved in this work suggests that the secondary structural diversity available to longer random RNAs may be required to activate transcription with high potency. Collectively these findings demonstrate that RNA is capable of folding into stable structures that present a compatible surface for recruiting the transcriptional machinery.

While we believe recruitment to be the most likely mechanism of action of these RNAs, we cannot rigorously exclude the possibility of a more complex activation mechanism such as one in which the RNA acts as a decoy for transcriptional inhibitors. However, the requirement of MS2 protein-mediated localization for activity, together with preliminary results indicating that deletion of specific recruitable components of the transcriptional machinery significantly decreases the activity of our RNAs (P. D. K., A. R. B., D. R. L., unpublished work), further supports simple recruitment as the mechanism of activation.

We found a surprisingly large fraction (~0.2%) of our initial random $N_{40}$ library was able to activate transcription. Our work parallels previous studies by Ptashne and co-workers that report 0.1% to 1% of short random peptides fused to a Gal4 DNA binding domain are capable of activating transcription (Lu, X., Ansari, A. Z., and Ptashne, M. (2000). An artificial transcriptional activating region with unusual properties. Proc Natl Acad Sci USA 97, 1988-1992; Ma, J., and Ptashne, M. (1987). A new class of yeast transcriptional activators. Cell 51, 113-119), although the most active peptide fusion was reported to activate transcription 1.6-fold as potently as intact Gal4. Given the significant differences between the physical properties of RNA and proteins, our results collectively imply that there are many different but comparably effective solutions for recruitment of the eukaryotic transcription initiation complex. This likely reflects both many possible targets as well as multiple sites per target for productive binding that leads to transcriptional activation. The fact that non-natural RNA-protein interactions can activate transcription lends further support to the recruitment model (Ptashne, M., and Gann, A. (1997). Transcriptional activation by recruitment. Nature 386, 569-577) by demonstrating that simple binding mechanisms distinct from those used in nature may be sufficient for mediating an important and ubiquitous biological function. RNA's lack of positive charges, ability to make hydrophobic interactions, and abundant negative charges—features found in protein transcriptional activators (Ponticelli, A. S., Pardee, T. S., and Struhl, K. (1995). The glutamine-rich activation domains of human Sp1 do not stimulate transcription in *Saccharomyces cerevisiae*. Mol Cell Biol 15, 983-988; Struhl, K. (1995). Yeast transcriptional regulatory mechanisms. Annu Rev Genet 29, 651-674)—apparently provide RNA with an effective chemical repertoire to interact with the transcriptional machinery.

Although the $N_{40}$ library yielded a high frequency of transcriptional activators, the $N_{80}$ library yielded significantly fewer. We initially hypothesized that a larger random region might offer a greater frequency of positives because of its much higher frequency of containing a specific required secondary structure (Wedel, A. B. (1996). Fishing the best pool for novel ribozymes. Trends Biotechnol 14, 459-465); this reasoning may hold true when comparing 40-base variable regions to the 10-base variable regions described by Ptashne and co-workers (Saha, S., Ansari, A., Jarell, K., and Ptashne, M. (2003). RNA sequences that work as transcriptional activating regions. Nucleic Acids Res 31, 1565-1570) that yielded a much lower frequency (~1 in $10^6$) of positives. Based on the 20-fold lower frequency and lower average activities of transcriptional activators in the $N_{80}$ library compared with the $N_{40}$ library, we additionally speculate that the smaller $N_{40}$ library balanced secondary structures required for high activity with minimizing the presence of unstructured single-stranded regions prone to intracellular degradation, and that at longer lengths, RNA instability can become limiting.

Our studies identify three regions within the most active evolved RNAs as particularly crucial for the observed activity. Gratifyingly, the sequence conservation within these regions, their predicted secondary structures, and the results of site-directed mutagenesis experiments are all consistent with a model in which these three subsequences (bases 17-19, 24-30, and 35-39) play key roles in transcriptional activation, possibly by forming essential base paired structures. Surprisingly, these findings suggest that extensive base pairing between the variable and constant regions is required for activity. The flanking constant regions, when paired with the variable sequences, may therefore provide a sufficiently large and well-ordered scaffold to enable effective interactions with the as yet unidentified target.

The approach to perturbing a biological function of interest (in this case, transcriptional activation) using RNA evolution in vivo requires an efficient selection or high throughput screen but is attractive because it does not require knowledge of any targets involved in the biological process of interest. In addition, while the more common RNA evolution approach of in vitro selection using previously identified and purified biological targets may not yield optimal desired activities when expressed in vivo, the approach described here evolves RNAs on the basis of their activities in natural cellular contexts. The well-characterized nature of several of the RNAs evolved in this study provide a promising start for efforts to identify the cellular target mediating RNA-based transcriptional activation using genetic or affinity-based methods. In addition, the identification of crucial bases within the evolved RNAs may enable the engineering of regulated RNA-based transcriptional activators that require the presence or absence of specific ligands. For example, it may be possible to evolve an RNA linker region that transduces a small molecule binding event (Soukup, G. A., and Breaker, R. R. (2000). Allosteric nucleic acid catalysts. Curr Opin Struct Biol 10, 318-325) into a conformational rearrangement in the critical stem region in order to either activate or repress transcription. In theory, this approach may also be used to study selectable or screenable functions unrelated to transcriptional activation.

Significance

We describe an approach to studying biological function using random RNA libraries coupled with in vivo selections. Using this approach we have evolved RNA transcriptional activators with potencies comparable to the most active natural protein-based activation domains such as VP16. The high frequency of finding active RNAs in our selection for transcriptional activators suggests that features of protein structure necessary for transcriptional activation can be mimicked effectively by nucleic acids. Additional rounds of diversification and selection, systematic site-directed mutagenesis, and secondary structure prediction together identified regions of the evolved RNA sequences that likely play important roles in transcriptional activation. Evolution of random RNA libraries in vivo may be a powerful tool for dissecting complex biological function.

Experimental Procedures

Yeast Strains and Media

Media consisted of yeast nitrogen base (Sigma), 4% dextrose, and synthetic drop out supplements lacking histidine or histidine and uracil (Clontech). Yeast were cultured either in liquid medium or on agar plates at 30° C. S. cerevisiae strains YBZ-1 (MATa, ura3-52, leu2-3, 112, his3-200, trp1-1, ade2, LYS2::(LexA op)-HIS3, ura3::(LexA op)-LacZ, LexA-MS2-MS2 coat (N55K)) and L40-ura3 (MATa, ura3-52, leu2-3112, his3Δ200, trp1Δ1, ade2, LYS2::(LexA op)-HIS3, ura3:: (LexA op)-LacZ) were a gift from Professor Marvin Wickens (Bernstein, D. S., Buter, N., Stumpf, C., and Wickens, M. (2002). Analyzing mRNA-protein complexes using a yeast three-hybrid system. Methods 26, 123-141).

Construction of Plasmids and RNA Libraries

Plasmids encoding the RNA libraries were based on the yeast shuttle vector pIIIa/MS2 (Bernstein, D. S., Buter, N., Stumpf, C., and Wickens, M. (2002). Analyzing mRNA-protein complexes using a yeast three-hybrid system. Methods 26, 123-141) (a gift from Professor Marvin Wickens). Library-encoding sequences were cloned directly into the plasmid using the unique SphI and XmaI sites. The plasmid carries a URA3 marker as well as the ADE2 gene that can be used to screen for false positives in the selection. Plasmid pIIIa/IRE-MS2 expresses a fusion of the Iron Response Element (IRE) and the MS2 hairpin (5'IRE-MS2-3') from the RPR promoter, and plasmid pAD-IRP expresses a fusion of the Iron Regulatory Protein (IRP) and the Gal4 activation domain driven from the ADH promoter. Random single stranded $N_{40}$ or $N_{80}$ libraries were generated on an Applied Biosystems Expedite 8909 DNA Synthesizer or purchased from Sigma-Genosys, respectively. Blunt-ended double stranded library inserts were synthesized by primer extension using the Klenow fragment of E. coli DNA Pol I from a constant primer binding site in the synthetic library oligonucleotides, digested with SphI and XmaI, and ligated into precut pIIIa/MS2 backbone to provide pIIIa/MS2-N40 and pIIIa/MS2-N80. Library-encoding plasmids were amplified by transformation into electrocompetent DH10B E. coli (Gibco/BRL) and isolated by plasmid purification. Constrained by the modest transformation efficiencies of yeast and our large variable region (40 bases), our libraries only cover a tiny fraction of possible sequence space even though the DNA encoding the library should contain >99% of sequences with >20% similarity to the N40-26 parent based on the analysis (Knight, R., and Yarus, M. (2003). Analyzing partially randomized nucleic acid pools: straight dope on doping. Nucleic Acids Res 31, e30) of Knight and Yarus.

LexA-VP16 was expressed from the ADH promoter on p416ADH-LV, a single copy yeast shuttle vector, to mimic the expression of LexA-MS2 in YBZ-1. LexA (1-202) was amplified from the LexA-Cyc8 plasmid, a gift from Kevin Struhl (Tzamarias, D., and Struhl, K. (1994). Functional dissection of the yeast Cyc8-Tup1 transcriptional co-repressor complex. Nature 369, 758-761), using the primers GGGGGGGGATCCCAGCCAGTCGCCGTTGCGAAT (SEQ ID NO: 55) and GGGGGGGCTAGCATGAAAGCGT-TAACGGCCAGG (SEQ ID NO: 56) and digested with BamHI and NheI. VP16 (residues 413-489) was amplified from the C7-VP16 plasmid, a gift of Roger Beerli (Beer R. R., Segal, D. J., Dreier, B., and Barbas, C. F., 3rd (1998). Toward controlling gene expression at will: specific regulation of the erbB-2/HER-2 promoter by using polydactyl zinc finger proteins constructed from modular building blocks. Proc Natl Acad Sci USA 95, 14628-1463), with the primers CCGC-CGGGATCCGCTCCCCCGACCGATGTCAGC (SEQ ID NO: 57) and CCGCCGCTCGAGTTAACCGTACTCGT-CAATTCCAAG (SEQ ID NO: 51) (designated VC), and digested with BamHI and XhoI. These digested fragments were ligated into Nhe I- and Xho I-digested pET23a vector (Novagen). The LexA-VP16 region was amplified from the resulting plasmid using the primer CCGCGGACTAGTAT-GAAAGCGTTAACGGCCAGGC (SEQ, ID NO: 59) and the primer VC above and subcloned into p416ADH (Mtunberg, D., Muller, R., and Funk, M. (1995). Yeast vectors for the controlled expression of heterologous proteins in different genetic backgrounds. Gene 156, 119-122), purchased from the ATCC) using SpeI and XhoI sites, All constructs were verified by DNA sequencing. Molecular biology enzymes were purchased from New England Biolabs.

Selection and Assay Protocol

For the selection experiments, the RNA expression plasmid was transformed into YBZ-1 using a standard lithium acetate procedure. Transformants were selected on media lacking histidine. Plasmid DNA was extracted via glass bead lysis and phenol extraction, ethanol precipitated, and then amplified in *E. coli*. Selection survivors were initially screened by restreaking on media lacking histidine and uracil prior to assaying. Selection at higher stringency was performed in an identical manner, with the addition of 1 mM 3-aminotriazole to the media.

Retransformed clones were assayed for β-galactosidase activity using a liquid o-nitrophenyl-β-galactopyranoside (ONPG) assay (Pryciak, P. M., and Hartwell, L. H. (1996). AKR1 encodes a candidate effector of the G beta gamma complex in the *Saccharomyces cerevisiae* pheromone response pathway and contributes to control of both cell shape and signal transduction. Mol Cell Biol 16, 2614-2626). Activity was calculated as Miller units and normalized to the Gal4 based positive control as explained in the figures. Assay values represent the average of at least three independent cultures of each clone.

Secondary Structure Prediction

Secondary structures of selected RNA sequences were individually predicted with the mfold program (Mathews, D. H., Sabina, J., Zuker, M., and Turner, D. H. (1999). Expanded sequence dependence of thermodynamic parameters improves prediction of RNA secondary structure. J Mol Biol 288, 911-940) using the most recent optimized parameters (predicted for 37° C.; these parameters are currently not available for 30° C.). Although the most thermodynamically stable structures were used in our analysis, all structures within 5% of the minimal energy were considered. For m26-11, the most stable predicted structure (shown in FIG. 5) is 5.6 kcal/mol more stable than the next lowest predicted structure.

Example 2

Engineering a Ligand-Dependent RNA Transcriptional Activator Introduction

RNA plays multiple roles in the cell as a carrier of genetic information, a catalyst of several crucial biological reactions (Doudna, J. A., and Cech, T. R. (2002). The chemical repertoire of natural ribozymes. Nature 418, 222-228), and a regulator of gene expression (Eddy, S. R. (2001). Non-coding RNA genes and the modern RNA world. Nat. Rev. Genet. 2, 919-929; Storz, G. (2002). An expanding universe of noncoding RNAs. Science 296, 1260-1263). The recent discovery of natural RNA sequences that bind to metabolites in vivo identified a new mechanism of regulation: small molecule-dependent translational inhibition mediated by RNA "riboswitches" (Winkler, W. C., and Breaker, R. R. (2003). Genetic control by metabolite-binding riboswitches. Chembiochem 4, 1024-1032). For example, Breaker and co-workers identified a riboswitch element in the 5'-untranslated region of several mRNAs coding for genes involved in thiamine biosynthesis in *E. coli* (Winkler, W., Nahvi, A., and Breaker, R. R. (2002). Thiamine derivatives bind messenger RNAs directly to regulate bacterial gene expression. Nature 419, 952-956). The TPP riboswitch consists of two domains: a TPP binding aptamer, and an "expression platform" that couples TPP binding to a conformational rearrangement that blocks the initiation of translation. The conservation of aptamer domains across species and the ability of these domains to bind ligand in the absence of the expression platform suggest that natural RNA aptamer domains are modular (Winkler, W. C., and Breaker, R. R. (2003). Genetic control by metabolite-binding riboswitches. Chembiochem 4, 1024-1032).

The creation of genetic switches can also benefit from the combination of modular components; eukaryotic transcription factors, for example, are amenable to engineering largely because of their DNA-binding and transcriptional activation domains are independent (Ptashne, M., and Gann, A. (1997). Transcriptional activation by recruitment. Nature 386, 569-577). The ability of RNA to form functional modules suggests an analogous approach to RNA-based switches that would regulate gene expression in response to the presence of a small molecule. The creation of such artificial switches requires two elements: the ability to bind a small molecule, and the ability to transmit that binding into downstream functional changes.

RNA possesses a number of attractive properties for use as a tool to regulate cellular function. Powerful in vitro evolution methods can rapidly identify RNA aptamers for a wide variety of proteins or small molecules of interest (Wilson, D. S., and Szostak, J. W. (1999). In vitro selection of functional nucleic acids. Annu. Rev. Biochem. 68, 611-647). Aptamers are capable of binding to their targets with very high specificity and affinity, and can be expressed in vivo (Famulok, M., and Verma, S. (2002). In vivo-applied functional RNAs as tools in proteomics and genomics research. Trends Biotechnol. 20, 462-466). For example, RNA aptamers against RNA polymerase II (Thomas, M., Chedin, S., Carles, C., Riva, M., Famulok, M., and Sentenac, A. (1997). Selective targeting and inhibition of yeast RNA polymerase II by RNA aptamers. J. Biol. Chem. 272, 27980-27986), NF-κB (Cassiday, L. A., and Maher, L. J., 3rd (2003). Yeast genetic selections to optimize RNA decoys for transcription factor NF-kappa B. Proc. Natl. Acad. Sci. USA 100, 3930-3935), RNA splicing factor B52 (Shi, H., Hoffman, B. E., and Lis, J. T. (1999). RNA aptamers as effective protein antagonists in a multicellular organism. Proc. Natl. Acad. Sci. USA 96, 10033-10038), and the σ2 subunit of human integrin (Blind, M., Kolanus, W., and Famulok, M. (1999). Cytoplasmic RNA modulators of an inside-out signal-transduction cascade. Proc. Natl. Acad. Sci. USA 96, 3606-3610) have been expressed in situ and have been shown to inhibit protein function in living eukaryotic cells. These developments suggest that RNA aptamers evolved in vitro can be used as probes to control and study biological function.

Breaker and co-workers have elegantly shown that catalytic RNAs can be evolved to acquire ligand dependence (Soukup, G. A., and Breaker, R. R. (2000). Allosteric nucleic acid catalysts. Curr. Opin. Struct. Biol. 10, 318-325). For example, the hammerhead ribozyme was engineered to cleave over a thousand times faster in the presence of theophylline (Soukup, G. A., Emilsson, G. A., and Breaker, R. R. (2000). Altering molecular recognition of RNA aptamers by allosteric selection. J. Mol. Biol. 298, 623-632). Similarly, Beal and co-workers evolved RNA aptamers that bind and inactivate the bacterial DNA-repair protein MutM in vitro in a manner that is blocked by neomycin (Vuyisich, M., and Beal, P. A. (2002). Controlling protein activity with ligand-regulated RNA aptamers. Chem. Biol. 9, 907-913). These examples suggest that evolutionary approaches are capable of generating and optimizing complex conformational shifts in RNA that link ligand binding to changes in function.

We recently evolved an RNA aptamer in *S. cerevisiae* that strongly activates transcription when tethered upstream of a reporter gene (Buskirk, A. R., Kehayova, P. D., Landrigan, A., and Liu, D. R. (2003). In vivo evolution of an RNA-based transcriptional activator. Chem. Biol. 10, 533-540). Here we report the development of a ligand-dependent transcriptional switch generated by fusion of the RNA transcriptional activator to a known small molecule aptamer, followed by the design and selection of a small library of linker regions. The basic mechanism of ligand dependence was confirmed by assaying a series of site-directed mutants. These findings demonstrate that RNA aptamers can be engineered to control biological function with synthetic small molecules in living cells.

Results

Design of a Ligand-Dependent Conformational Shift

The creation of an RNA-based transcriptional switch requires that a functional RNA acquire both small-molecule binding activity and a small-molecule dependent conformational equilibrium that transduces binding into altered function. As the starting point for our engineering efforts, we used an RNA that we previously evolved in S. cerevisiae to activate transcription (Buskirk, A. R., Kehayova, P. D., Landrigan, A., and Liu, D. R. (2003). In vivo evolution of an RNA-based transcriptional activator. Chem. Biol. 10, 533-540). Characterization of one of the strongest activators, m26-11, suggested three regions that participate in base pairing (bases 16-18, 23-33, and 35-38) and are required for transcriptional activation (FIG. 6A). In contrast, bases 1-15 are predicted to not interact with essential secondary structural elements, are not conserved among related activators, and can be mutated with little effect on function.

Figure 7:
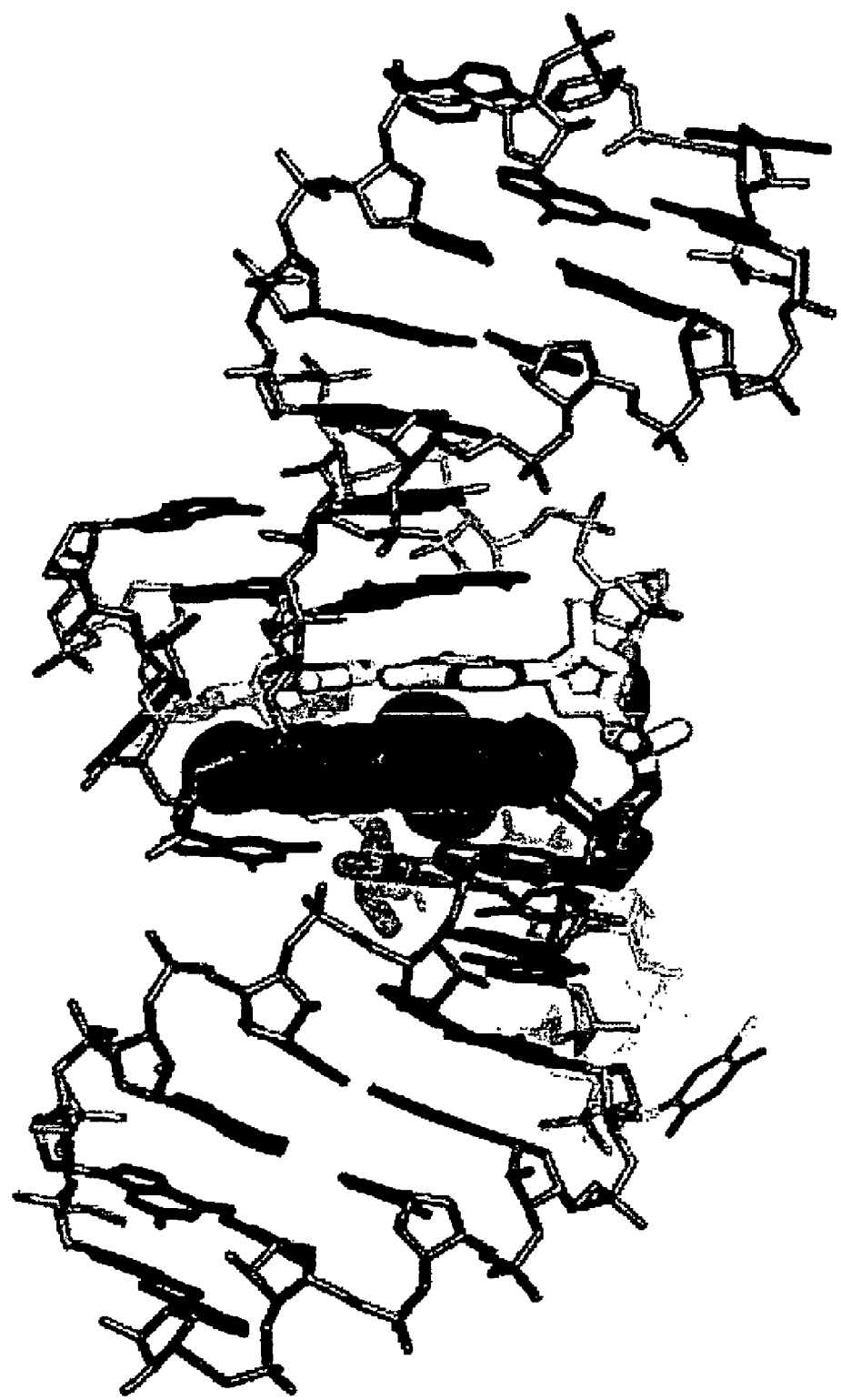
FIG. 7 shows the structure of TMR-binding aptamer bound to TMR (Baugh, C., Grate, D., and Wilson, C. (2000). 2.8 A crystal structure of the malachite green aptamer. J. Mol. Biol. 301, 117-128). TMR is shown in red, the C1-G23 base pair in orange, and the G2-C22 base pair in yellow. Rendered with Pymol.

We sought a well-characterized small molecule-binding aptamer to insert into the nonconserved region of m26-11. An aptamer selected by Wilson and co-workers (Grate, D., and Wilson, C. (1999). Laser-mediated, site-specific inactivation of RNA transcripts. Proc. Natl. Acad. Sci. USA 96, 6131-6136) binds tetramethylrosamine (TMR), an aromatic intercalator (FIG. 6B), with high affinity ($K_d$=40 nM) (Baugh, C., Grate, D., and Wilson, C. (2000). 2.8 A crystal structure of the malachite green aptamer. J. Mol. Biol. 301, 117-128). TMR is known to cross the S. cerevisiae cell wall and is non-toxic to yeast at concentrations up to 1 µM (Grate, D., and Wilson, C. (2001). Inducible regulation of the S. cerevisiae cell cycle mediated by an RNA aptamer-ligand complex. Bioorg. Med. Chem. 9, 2565-2570). Positions in the aptamer crucial for ligand binding have been identified by site-directed mutagenesis and X-ray crystallography (Baugh, C., Grate, D., and Wilson, C. (2000). 2.8 A crystal structure of the malachite green aptamer. J. Mol. Biol. 301, 117-128). The structure reveals that the TMR-binding loops form two C:G base pairs that stack on either side of the bound ligand (FIG. 7). Ligand binding stabilizes these base pairs, orders the loops, and increases the stability of the helices at either end of the aptamer. These conformational changes suggest a strategy for linking TMR binding to the activity of the m26-11 transcriptional activator.

We previously showed that mutation of m26-11 bases 17 or 18 from C to A led to a 10 to 20-fold reduction in transcriptional activation (Buskirk, A. R., Kehayova, P. D., Landrigan, A., and Liu, D. R. (2003). In vivo evolution of an RNA-based transcriptional activator. Chem. Biol. 10, 533-540). Based on structural models, we proposed that these two conserved bases, together with C19, form key C:G base pairs that stabilize a secondary structure required for activity (FIG. 6A) (Zuker, M. (2003). Mfold web server for nucleic acid folding and hybridization prediction. Nucleic Acids Res. 31, 3406-3415). We hypothesized that when bases 1-16 of m26-11 are replaced with the core of the TMR aptamer (bases 6-33), the flexibility of the unliganded loops would destabilize these three C:G base pairs and render the RNA inactive. Upon TMR binding, the loops may become more ordered, stabilizing these key base-pairing interactions within m26-11 (FIG. 6B) and restoring transcriptional activation activity.

Selection and Screening to Optimize Ligand Dependence

Since it is difficult to predict the optimal linker sequence that would efficiently transduce TMR binding to the restoration of m26-11 function, we randomized seven nucleotides on one strand in the linker region (shown in green in FIG. 6B), including the bases predicted to be involved in the key secondary structure (27-29). DNA oligonucleotides containing the TMR aptamer sequence fused to the activator through seven randomized linker nucleotides were cloned into an m26-11 RNA expression vector as previously described (Buskirk, A. R., Kehayova, P. D., Landrigan, A., and Liu, D. R. (2003). In vivo evolution of an RNA-based transcriptional activator. Chem. Biol. 10, 533-540). The library was amplified in E. coli ($1\times10^6$ transformants providing full coverage of the theoretical diversity of $1.6\times10^4$ linkers) and used to transform S. cerevisiae selection strain YBZ-1. This yeast strain contains HIS3 and lacZ reporter genes downstream of lexA operator sites and expresses a LexA-MS2 coat protein fusion that localizes our RNA construct to these reporter genes (Bernstein, D. S., Buter, N., Stumpf, C., and Wickens, M. (2002). Analyzing mRNA-protein complexes using a yeast three-hybrid system. Methods 26, 123-141). RNAs that are capable of transcriptional activation enable the cells to grow in the absence of histidine and to express β-galactosidase.

YBZ-1 cells expressing the RNA library ($1\times10^5$ transformants) were plated onto media lacking histidine and containing 1 µM TMR. Selection plates also contained varying amounts of 3-aminotriazole (0, 0.2, or 1.0 mM 3-AT), a competitive inhibitor of His3p activity, to increase the stringency of the selection. Several thousand colonies grew without any 3-AT, several hundred colonies grew in the presence of 0.2 mM 3-AT, and ~50 colonies grew robustly at the highest stringency (1 mM 3-AT).

To assess whether these surviving clones encoded ligand-dependent transcriptional activators, 50 robust colonies and 60 smaller colonies surviving the selection with 1 mM 3-AT were replated onto fresh selection media in the presence or absence of TMR. Of the 110 colonies screened in this manner, 17 displayed promising phenotypes by growing more readily in the presence of TMR than in its absence. After confirmation of positives by retransformation and plating, four unique clones (clones 19, 32, 77, and 96) exhibited substantially faster growth in the presence of TMR, further suggesting that transcriptional activation was increased by ligand binding. Indeed, clone 96 showed no growth in the absence of TMR in media lacking histidine and containing 1 mM 3-AT (FIG. 8A).

To further characterize the selected clones, cultures of clones 19, 32, 77, 96 and m26-11 (without the TMR aptamer as a control) in YBZ-1 were assayed for β-galactosidase activity after growing 24 h either in the absence or presence of 1 µM TMR. The presence of TMR did not affect transcriptional activation by m26-11, confirming that TMR alone does not influence transcription of the reporter gene (FIG. 8B). Clones 19 and 32 exhibited only modest ligand-dependent activation ($\leq$1.6-fold higher β-galactosidase activity in the presence of TMR). Clone 19 maintained the level of activity seen with m26-11 and was slightly enhanced upon TMR binding; clone 32, however, showed much weaker activity even in the presence of TMR (data not shown). Two clones demonstrated stronger levels of TMR dependence: clone 77 was activated 2.3-fold, while clone 96 was 10.3-fold more active in the presence of TMR (FIG. 8B). Both of these clones exhibited reduced activity in the absence of TMR and potent transcriptional activation, comparable to that of m26-11, upon addition of TMR.

Sequence analysis revealed that the conserved CCC sequence (bases 16-18 in m26-11; bases 27-29 in clone 96) in three of the above selectants (clones 19, 77, and 96) was mutated to CCU (Table 2). Secondary structure prediction using the mfold algorithm (Zuker, M. (2003). Mfold web server for nucleic acid folding and hybridization prediction. Nucleic Acids Res. 31, 3406-3415) suggests that CCU can replace the conserved CCC sequence and pair with GGG (bases −3 to −1; hereafter all base numbers are from clone 96, FIG. 6B) to maintain the key interaction present in the original m26-11 aptamer. We hypothesize that the introduction of the G-U wobble pair destabilizes this pairing enough to significantly lower transcriptional activation potency, as evidenced by the lower activity of the selected clones in the absence of TMR compared with that of m26-11. In the presence of TMR, the loops of the aptamer are ordered by the formation of two C:G base pairs (C1:G23 and G2:C22) surrounding TMR, stabilizing duplex structure in this region (FIG. 6B). This stabilization enhances pairing of the CCU-containing region, restoring function. The single nucleotide change of C29 to U is not sufficient for maximum observed ligand dependence since clones 96, 77, and 19 each contain this mutation but display varying degrees of activity and ligand dependence. These results highlight the advantages of an evolutionary approach that can simultaneously optimize complex and interconnected conformational changes that occur upon small-molecule binding.

tivation of RNA transcripts. Proc. Natl. Acad. Sci. USA 96, 6131-6136; Baugh, C., Grate, D., and Wilson, C. (2000). 2.8 A crystal structure of the malachite green aptamer. J. Mol. Biol. 301, 117-128); similarly, mutant m96-3 mutates a critical A (base 21) in this binding loop to C. If TMR binding occurs in a manner similar to that of the isolated aptamer and is necessary for the observed ligand dependence, then both of these mutants should not be activated upon addition of ligand. Mutants m96-2 and m96-3 indeed exhibit the same low activity as clone 96 in the absence of ligand, and addition of TMR does not further activate transcription (FIG. 8B). These findings indicate that TMR binding is required for the observed ligand dependence of the clone 96 RNA.

Figure 9:
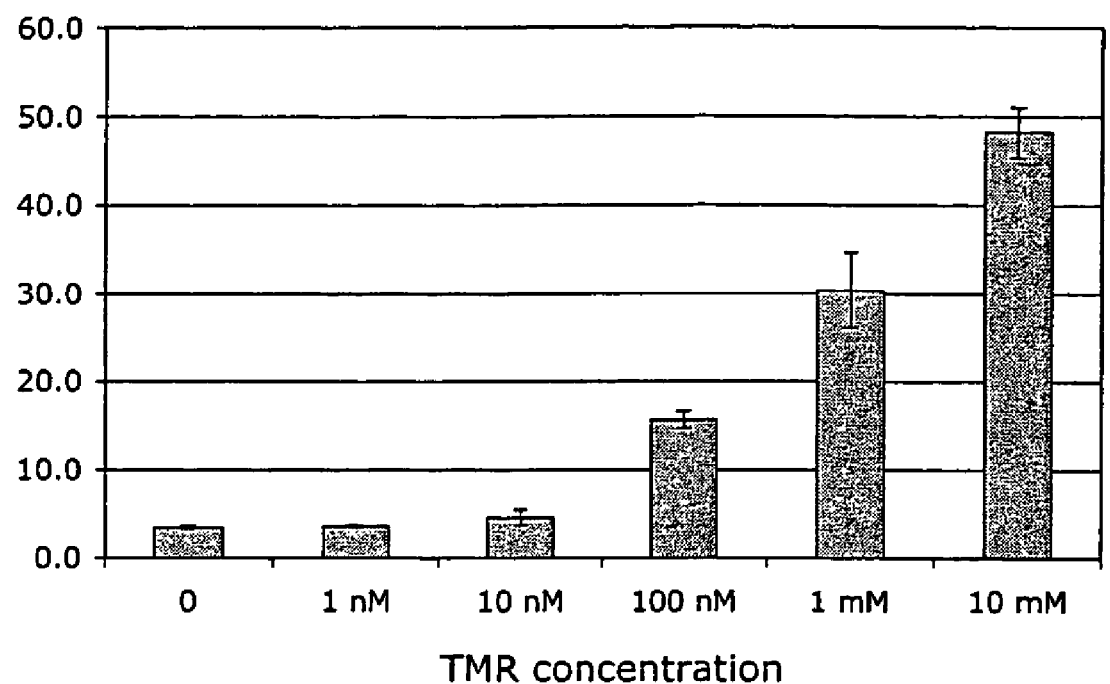
FIG. 9 demonstrates the dose-dependent response of a ligand-dependent RNA transcriptional activator. *S. cerevisiae* expressing the clone 96 RNA were grown in varying concentrations of TMR and assayed quantitatively for β-galactosidase activity. Error bars represent the range of values from two independent trials.

To explore further the properties of clone 96, we determined the dose-dependence of transcriptional activation by growing cultures expressing clone 96 in the presence of varying concentrations of TMR ranging from 1 nM to 10 μM. As seen in FIG. 9, transcriptional activation increases gradually with higher concentrations of TMR. These results further support the conclusion that TMR increases levels of transcriptional activation through specific binding to the RNA activation domain and modulation of its function.

TABLE 2

Sequences of TMR-dependent activators. Nucleotides 1-16 of m26-11 were replaced with bases 6-33 of the TMR aptamer (bold). Essential positions in m26-11 are italicized. The randomized linker region (bases 27-33) is shown in italics. Site-directed mutations introduced into clone 96 are underlined.

```
Clone # Sequence m26-11   CGCGCGAGUAUACUCC----------CCCAAGC-GGAUGCCUAAGCCUCUU (SEQ ID NO: 48)

19                1    1    2    2    3    3    4    4    5
         1   5    0    5    0    5    0    5    0    5    0
         CGACUGGCGAGAGCCAGGUAACGAAUCCUGGGU-GGAUGCCUAAGCCUCUU (SEQ ID NO: 61)

32       CGACUGGCGAGAGCCAGGUAACGAAUCCGGGCA-GGAUGCCUAAGCCUCUU (SEQ ID NO: 62)

77       CGACUGGCGAGAGCCAGGUAACGAAUCCUUACGCGGAUGCCUAAGCCUCUU (SEQ ID NO: 63)

96       CGACUGGCGAGAGCCAGGUAACGAAUCCUAACC-GGAUGCCUAAGCCUCUU (SEQ ID NO: 64)

96 mut-1 CGACUGGCGAGAGCCAGGUAACGAAUCCCAACC-GGAUGCCUAAGCCUCUU (SEQ ID NO: 65)
U29C 96 mut-2 CGACUGGCGAGAGCCAGGUAAAGAAUCCUAACC-GGAUGCCUAAGCCUCUU (SEQ ID NO: 66)
C22A 96 mut-3 CGACUGGCGAGAGCCAGGUACCGAAUCCUAACC-GGAUGCCUAAGCCUCUU (SEQ ID NO: 67)
A21C
```

Mechanism and Properties of Ligand-Dependent Activators

To test our hypothesis about the importance of the predicted wobble pair and to demonstrate that TMR binding is necessary for the observed ligand dependence, we prepared three site-directed mutants of clone 96, the most highly ligand-dependent transcriptional activator. Mutant m96-1 reverts U29 (in CCU) to CCC to test the role of the wobble pair. The above model predicts that m96-1 should be highly active but much less dependent on TMR. Indeed, β-galactosidase assays of m96-1 revealed that its absolute activity is similar to that of activated clone 96, but that it is much less dependent on ligand (1.8-fold instead of 10.3-fold for clone 96, FIG. 8B).

Mutant m96-2 contains a C22 to A mutation in the TMR binding loop that is predicted to abolish TMR binding (Grate, D., and Wilson, C. (1999). Laser-mediated, site-specific inac- Discussion The creation of small molecule-dependent transcriptional switches provides researchers with the ability to regulate biological function with precisely chosen inputs. By appending a known RNA aptamer to a functional RNA and using in vivo selection methods to evaluate a library of possible linker sequences, we created an entirely artificial ligand-activated transcriptional activation domain. This work represents to our knowledge the first example of engineering ligand dependence into an activation domain, and of using small molecule-regulated RNA aptamers to modulate biological function in vivo.

In vivo selection and screening for ligand dependence yielded a transcriptional activator that displays a 10-fold increase in activity in the presence of a cell-permeable small molecule, tetramethylrosamine. In this mutant, a critical three base pair structural element was mutated from CCC (base 27-29) to CCU. We propose that the weaker wobble pair destabilizes this structure, allowing the unliganded TMR aptamer to force the activator sequence into a non-functional conformation. Upon binding of ligand, the TMR aptamer is ordered, with increased helical structure, forcing the CCU sequence at base 27-29 to pair with GGG (base −3 to −1) to form an active conformation. As predicted by this model, reversal of this critical CCU to the original CCC sequence increases activity but reduces ligand dependence.

The randomized bases at positions 30-33 also must play a role, since three clones with the CCU at positions 27-29 but differing at 30-33 were shown to have different degrees of ligand dependence. Consistent with this analysis, only about 3% of the RNA subpopulation containing CCU at bases 27-29 survived the initial selection. Positions 30-33 are predicted to form a bulge and can be mutated with little or no effect in the m26-11 context. In the TMR aptamer fusions these bases may stabilize inactive conformations (through base pairing) in the unliganded structure and thereby influence the conformational equilibrium without altering the ligand-bound secondary structure. The use of in vivo selection techniques therefore identified both the wobble pair and additional optimal sequences that collectively couple ligand binding with increased transcriptional activation.

The success of our design strategy highlights the power of methods available for the manipulation of RNA. Mutagenesis studies and secondary structural prediction tools provided a model of both the structure and key functional determinants in our previously evolved RNA activation domains. This information suggested that a non-essential sequence element could be replaced with a small molecule aptamer, and that the structure could be disrupted in a predictable manner to regulate function. Together with directed evolution techniques, these tools provide powerful engineering capabilities for functional RNAs. The lack of high-resolution structural prediction tools makes analogous engineering efforts in proteins more difficult.

These results suggest a general approach to the creation of RNA-based probes of biological function than can be regulated by small molecules. As methods exist to create RNA aptamers against a wide variety of proteins of interest, it may be possible to evolve RNA inhibitors of protein function and engineer them to be regulated by a ligand such as TMR. There may be some situations in which it is easier to discover an RNA that inhibits protein function than a small molecule that does the same job directly. Small molecule modulators of protein function are difficult to find for proteins that lack natural small molecule-binding sites or that participate in protein-protein interactions (Berg, T. (2003). Modulation of protein-protein interactions with small organic molecules. Angew. Chem. Int. Ed. Engl. 42, 2462-2481). The ability of RNA to bind to both small-molecule and protein targets with high affinity and specificity may allow their use as ligand-dependent switches to dissect genetic pathways and elucidate gene function. In addition, the observed dose-dependence of clone 96 in response to TMR highlights an advantage of small molecule-based approaches over purely genetic approaches to studying biological function: activity can be fine-tuned by varying the concentration of small-molecule inducer.

The ease with which two pre-existing RNAs can be functionally linked has evolutionary implications for the creation of novel ligand-dependent RNAs. Small molecule- and macromolecule-binding RNA structures can be modularly combined, analogously to domain swapping in protein evolution, to rapidly generate new functions. In a striking example recently reported by Breaker and co-workers (Winkler, W. C., Nahvi, A., Roth, A., Collins, J. A., and Breaker, R. R. (2004). Control of gene expression by a natural metabolite-responsive ribozyme. Nature 428, 281-286), a natural RNA regulates gene expression at the translation level by linking the binding of a cellular metabolite to self-cleavage of the glmS mRNA. Consistent with the findings of Breaker and co-workers, our results suggest that RNA functional elements may have combined in simple ways to serve as sophisticated genetic control systems before the advent of modern protein-based regulation. In addition, the creation of an activator of transcription that is dependent on a specific cell-permeable synthetic small molecule increases the scope of known RNA regulatory activity, which has been primarily limited to repression of gene expression (Eddy, S. R. (2001). Non-coding RNA genes and the modern RNA world. Nat. Rev. Genet. 2, 919-929; Winkler, W. C., and Breaker, R. R. (2003). Genetic control by metabolite-binding riboswitches. Chembiochem 4, 1024-1032).

Significance

The development of small molecule-dependent switches can facilitate the regulation and study of biological function. We engineered a transcriptional switch from two modular RNA elements: a known small molecule-binding aptamer and an RNA-based transcriptional activation domain. Prior structure-function studies and secondary structural prediction enabled the successful design of a conformational shift upon ligand binding, which was functionally optimized by selection in living cells. The resulting RNA transcriptional activation domain displays 10-fold higher activity in the presence of the cell-permeable small molecule tetramethylrosamine. Our results highlight the strengths of tools available for engineering RNA structure and function. The method of generating aptamers to a protein target of interest and appending a small molecule-binding aptamer may serve as a general approach to creating small molecule-dependent regulators of biological function in living cells. The ability of RNA to activate transcription in a ligand-dependent manner adds to the known repertoire of gene regulation by RNA and hints at the versatility of modular RNA elements that may have played a role in regulating macromolecular function in an ancient RNA world.

Experimental Procedures

Yeast Strains and Media

Media consisted of yeast nitrogen base (Sigma), 4% dextrose, and synthetic drop out supplements lacking histidine or uracil (Clontech). Yeast were cultured at 30° C. Strain YBZ-1 (MATa, ura3-52, leu2-3,112, his3-200, trp1-1, ade2, LYS2:: (LexA op)-lacZ, LexA-MS2-MS2 coat (N55K)) was a gift from Prof. Marvin Wickens (Bernstein, D. S., Buter, N., Stumpf, C., and Wickens, M. (2002). Analyzing mRNA-protein complexes using a yeast three-hybrid system. Methods 26, 123-141). Tetramethylrosamine was purchased from Molecular Probes and 3-aminotriazole was purchased from Sigma.

Construction of RNA Library and Mutants

Plasmids expressing the RNA activator m26-11 and its derivatives were based on the yeast shuttle vector pIIIa/MS2 (Bernstein, D. S., Buter, N., Stumpf, C., and Wickens, M. (2002). Analyzing mRNA-protein complexes using a yeast three-hybrid system. Methods 26, 123-141). Library-encoding sequences were cloned directly into plasmids using unique SphI and XmaI sites. Fusion of the TMR aptamer and m26-11 sequence connected by seven randomized nucleotides was accomplished using the following degenerate oligonucleotide: 5'-CGCGCGGCATGCAAGAGGCTTAG-GCATCNNNNNNNATTCGT TACCTGGCTCTCGCCAGTCGCCCGG-GACGCCGACGCC-3'(SEQ ID NO: 68) synthesized on an Applied Biosystems Expedite 8909 DNA Synthesizer. Blunt-ended double stranded library inserts were generated by primer extension using the Klenow fragment of DNA Pol I from a constant primer binding site on the library oligonucleotides, digested with SphI and XmaI, and ligated into precut pIIIa/MS2 backbone. Library-encoding plasmids were amplified in *E. coil* DH10B and isolated via plasmid purification.

Three mutants of clone 96 were generated by DNA synthesis of both strands incorporating the relevant mutation, followed by annealing, digestion, and ligation as described above. All constructs were verified by DNA sequencing using Applied Biosystems Big-Dye Terminator 3.0 kits. Molecular biology enzymes were purchased from New England Biolabs.

Selection and Assay Protocol

For the selection experiments, the RNA expression plasmid was transformed into YBZ-1 using a standard lithium acetate protocol. Transformants were selected on media lacking histidine and containing 0, 0.2, or 1 mM 3-aminotriazole (3-AT) to increase stringency. Plasmid DNA was extracted from selectants by glass bead lysis and phenol extraction, ethanol precipitated, and amplified in *E. coli*. Selection survivors were initially screened by replating on media lacking histidine, containing 1 mM 3-AT, and containing either no TMR or 1 μM TMR. Retransformed clones were grown on media lacking uracil with or without TMR and assayed in triplicate for β-galactosidase activity using liquid o-nitrophenyl-β-galactopyranoside (ONPG) as described (Pryciak, P. M., and Hartwell, L. H. (1996). AKR1 encodes a candidate effector of the G beta gamma complex in the *Saccharomyces cerevisiae* pheromone response pathway and contributes to control of both cell shape and signal transduction. Mol. Cell. Biol. 16, 2614-2626). Activity was calculated as Miller units. Slight growth inhibition was seen at 10 μM TMR (see FIG. 9).

OTHER EMBODIMENTS

Those of ordinary skill in the art will readily appreciate that the foregoing represents merely certain preferred embodiments of the invention. Various changes and modifications to the procedure and compositions described above can be made without departing from the spirit or scope of the present invention, as set forth in the following claims.

What is claimed is:

1. An isolated transcriptional regulator comprising an RNA molecule, wherein the RNA molecule comprises a sequence having at least 80% homology with the sequence set forth as GGAUGCCUAAGCCUCUU (SEQ ID NO: 22), and wherein when the RNA molecule is recruited upstream of a gene, transcription of the gene is increased.

2. The isolated transcriptional regulator of claim 1, wherein the transcription of the gene is increased 2-fold.

3. The isolated transcriptional regulator of claim 1, wherein the transcription of the gene is increased 10-fold.

4. The isolated transcriptional regulator of claim 1, wherein the transcription of the gene is increased 50-fold.

5. The isolated transcriptional regulator of claim 1, wherein the transcription of the gene is at least as high as a three-hybrid positive control using a natural yeast Gal4 activation domain.

6. The isolated transcriptional regulator of claim 1, wherein the transcription of the gene is at least 10-fold higher than a three-hybrid positive control using a natural yeast Gal4 activation domain.

7. The isolated transcriptional regulator of claim 1, wherein the transcription of the gene is approximately 50-fold higher than a three-hybrid positive control using a natural yeast Gal4 activation domain.

8. The isolated transcriptional regulator of claim 1, wherein the transcription of the gene is approximately two-fold lower than a three-hybrid positive control using natural VP16 activation domain.

9. The isolated transcriptional regulator of claim 1 further comprising an MS2 hairpin that binds to an MS2 coat protein or LexA-MS2 coat protein fusion protein.

10. The isolated transcriptional regulator of claim 1 further comprising an element capable of associating with a DNA-binding protein, wherein the DNA-binding protein is a LexA-MS2 coat protein fusion protein.

11. The isolated transcriptional regulator of claim 1, wherein the RNA molecule comprises a sequence selected from the group consisting of:

```
                                                    (SEQ ID NO: 23)
m26-10  CGCGGAAGAAUGAUCCCCCAAGUGGAUGCCUAAGCCUCUU;

(SEQ ID NO: 24)
m26-36  CGCGGAAGAAUUCUCCCCCAAGUGGAUGCCUAAGCCUCUU;

(SEQ ID NO: 25)
m26-31  CGCGGAAGAAUGCUCCCCCGAGUGGAUGCCUAAGCCUCAU;

(SEQ ID NO: 26)
m26-9   CGCGGAGGAAUGCUCCCCCGAGUGGAUGCCUAAUCCUCUU;

(SEQ ID NO: 27)
m26-14  CGCGGAAGCAUACUCCCCCGAGUGGAUGCCUAAGCCUCUU;

(SEQ ID NO: 28)
m26-15  CGCGGACCAAUGGUCCCCCAAGUGGAUGCCUAAGCCUCUU;

(SEQ ID NO: 29)
m26-34  CGCGGAAGAUUGCCCCCCAAGUGGAUGCCUAAACCUCUA;

(SEQ ID NO: 30)
m26-29  CGCGGAAGAUUGUUCCCCCAAGUGGAUGCCUAAACCUCAU;

(SEQ ID NO: 31)
m26-28  CGCGGAAAAUACUCCCCCAAGUGGAUGCCUAAACCUAUU;

(SEQ ID NO: 32)
m26-17  CGCGGAAGAAUGAUCCCCCAGGUGGAUGCCUAAGCCUCUA;

(SEQ ID NO: 33)
m26-30  CGCGGAACAAUGCUCCCCCAGCUGGAUGCCUAAGCCUCUA;

(SEQ ID NO: 34)
m26-20  CGGGGAAGAAUGCUGCCCAAAGUGGAUGCCUAAGCCUCUU;

(SEQ ID NO: 35)
m26-4   CGCGGAAGAAUGCUGCCCAACCUGGAUGCCUAAACCUCUU;

(SEQ ID NO: 36)
m26-32  CGCGGAAGAAUGCUGCCCAACCUGGAUGCCUAAACCUCUU;

(SEQ ID NO: 37)
m26-13  CUCGGAACAAUGCCCCCCAAGUGGAUGCCUAAACCUCAU;
```

-continued

```
                                                    (SEQ ID NO: 38)
m26-35    CUCGGAAGAAUUCUCCCGAUAGUGGAUGCCUAAGCCUCUU;

(SEQ ID NO: 39)
m26-16    CGCGGAAGAAGAGUCCCCCGAGUGGAUGCCUAAACCUCUU;

(SEQ ID NO: 40)
m26-18    CGCGGAACAAUGUUGCCCCAAAUGGAUGCCUAAGCCUCUU;

(SEQ ID NO: 41)
m26-25    CGCGGAAGAACACUCCCCCACGUGGAUGCCUAAGCCUCCUU;

(SEQ ID NO: 42)
m26-21    CGCGGAAGACUGCAGCCCCAGGUGGAUGCCUAAACCUCGGU;

(SEQ ID NO: 43)
m26-39    CCCGGAAGACUGCAGCCCCAGGUGGAUGCCUAAACCUCUU;

(SEQ ID NO: 44)
m26-33    CGCGGAAGACUUCAGCCCCAAGUGGAUGCCUAAGCCUCUUA;

(SEQ ID NO: 45)
m26-1     CGCGGGUGUAAGCCCCCCAGGUGGAUGCCUAAGCCUCUU;

(SEQ ID NO: 46)
m26-23    CGCGUAAACAUGCGGCCCCAAGUGGAUGCCUAAGCCUCCU;

(SEQ ID NO: 47)
m26-24    CGCGGAAAGAUGAUCACCCGAGUGGAUGCCUAAGCCUCUU;

(SEQ ID NO: 48)
m26-11    CGCGCGAGUAUACUCCCCCAAGCGGAUGCCUAAGCCUCUU;

(SEQ ID NO: 49)
m26-19    CGCAGAAGAUACCUCCCCCAAGUGGAUGCCUAAGCCUCAU;

(SEQ ID NO: 50)
m26-26    AACAGAAGAAUACUCCCCAAGUGGAUACCUAAGCAUCUU;

(SEQ ID NO: 51)
m26-37    CGCGGAAAAAUUCUUCCCCCAAGUGGAUGCCUAAGCCUCUU;

(SEQ ID NO: 52)
m26-38    CGCGGAAAAAUUCUUCCCCCAAGUGGAUGCGUAAGCCUCUU;

(SEQ ID NO: 53)
m26-7     CGCGGAAGAACGCUCCCCGACGUGGAUGCCUAUUGUCCUU;
and (SEQ ID NO: 54)
con-      CGCGGAAGAAUGCUCCCCCAAGUGGAUGCCUAAGCCUCUU.
sensus
```

12. The isolated transcriptional regulator of claim 1, wherein the RNA molecule comprises the sequence:

```
    consensus                         (SEQ ID NO: 54)
    CGCGGAAGAAUGCUCCCCCAAGUGGAUGCCUAAGCCUCUU.
```

13. The isolated transcriptional regulator of claim 1, wherein the RNA molecule comprises the sequence:

```
                                                    (SEQ ID NO: 30)
m26-29    CGCGGAAGAUUGUUCCCCCAAGUGGAUGCCUAAACCUCAU.
```

14. The isolated transcriptional regulator of claim 1, wherein the RNA molecule comprises the sequence:

```
                                                    (SEQ ID NO: 48)
m26-11    CGCGCGAGUAUACUCCCCCAAGCGGAUGCCUAAGCCUCUU.
```

15. The isolated transcriptional regulator of claim 1, wherein the RNA molecule comprises a sequence responsible for transcriptional regulation that ranges from 20-50 bases in length.

16. The isolated transcriptional regulator of claim 1, wherein the gene is HIS 3.

17. The isolated transcriptional regulator of claim 1, wherein the gene is LacZ.

18. The isolated transcriptional regulator of 1 comprising the tetramethylrosamine (TMR)-binding aptamer of sequence:

```
CGACUGGCGAGAGCCAGGUAACGAAU.    (SEQ ID NO: 70)
```

19. The isolated transcriptional regulator of claim 1 further comprising an RNA molecule comprising a sequence selected from the group consisting of:

```
                                                    (SEQ ID NO: 61)
CGACUGGCGAGAGCCAGGUAACGAAUCCUGGGUGGAUGCCUAAGCCUCUU;

(SEQ ID NO: 62)
CGACUGGCGAGAGCCAGGUAACGAAUCCGGGCAGGAUGCCUAAGCCUCUU;

(SEQ ID NO: 63)
CGACUGGCGAGAGCCAGGUAACGAAUCCUUACGCGGAUGCCUAAGCCUCU
U;

(SEQ ID NO: 64)
CGACUGGCGAGAGCCAGGUAACGAAUCCUAACCGGAUGCCUAAGCCUCUU;

(SEQ ID NO: 65)
CGACUGGCGAGAGCCAGGUAACGAAUCCCAACCGGAUGCCUAAGCCUCUU;

(SEQ ID NO: 66)
CGACUGGCGAGAGCCAGGUAAAGAAUCCUAACCGGAUGCCUAAGCCUCUU;
and (SEQ ID NO: 67)
CGACUGGCGAGAGCCAGGUACCGAAUCCUAACCGGAUGCCUAAGCCUCUU.
```

20. An isolated vector encoding the transcriptional regulator of claim 1.

21. The isolated vector of claim 20 further comprising an RNase P RNA gene (RPR) promoter.

22. The isolated vector of claim 20 further comprising an RNase P RNA gene (RPR) terminator.

23. The isolated vector of claim 20, wherein the vector is a plasmid.

24. The isolated vector of claim 23, wherein the plasmid can be propagated in yeast.

25. The isolated vector of claim 23, wherein the plasmid is derived from yeast shuttle vector pIIIa/MS2.

26. The isolated vector of claim 23, wherein the plasmid includes marker genes.

27. The isolated transcriptional regulator of claim 1, wherein the RNA molecule comprises a sequence having at least 80% homology with a sequence selected from the group consisting of:

```
CCCAAGUGGAUGCCUAAGCCUCUU;        (SEQ ID NO: 60)
CCCAAGCGGAUGCCUAAGCCUCUU;        (SEQ ID NO: 69)
and
CCCAACCGGAUGCCUAAGCCUCUU.        (SEQ ID NO: 71)
```

28. The isolated transcriptional regulator of claim 1, wherein the RNA molecule comprises a sequence having at least 90% homology with a sequence selected from the group consisting of:

```
CCCAAGUGGAUGCCUAAGCCUCUU;    (SEQ ID NO: 60)
CCCAAGCGGAUGCCUAAGCCUCUU;    (SEQ ID NO: 69)
and
CCCAACCGGAUGCCUAAGCCUCUU.    (SEQ ID NO: 71)
```

29. The isolated transcriptional regulator of claim 1, wherein the RNA molecule comprises a sequence having at least 95% homology with a sequence selected from the group consisting of:

```
CCCAAGUGGAUGCCUAAGCCUCUU;    (SEQ ID NO: 60)
CCCAAGCGGAUGCCUAAGCCUCUU;    (SEQ ID NO: 69)
and
CCCAACCGGAUGCCUAAGCCUCUU.    (SEQ ID NO: 71)
```

30. The isolated transcriptional regulator of claim 1, wherein the RNA molecule comprises a sequence having up to 1 nucleotide mismatch with a sequence selected from the group consisting of:

```
CCCAAGUGGAUGCCUAAGCCUCUU;    (SEQ ID NO: 60)
CCCAAGCGGAUGCCUAAGCCUCUU;    (SEQ ID NO: 69)
and
CCCAACCGGAUGCCUAAGCCUCUU.    (SEQ ID NO: 71)
```

31. The isolated transcriptional regulator of claim 1, wherein the RNA molecule comprises a sequence selected from the group consisting of:

```
CCCAAGUGGAUGCCUAAGCCUCUU;    (SEQ ID NO: 60)
CCCAAGCGGAUGCCUAAGCCUCUU;    (SEQ ID NO: 69)
and
CCCAACCGGAUGCCUAAGCCUCUU.    (SEQ ID NO: 71)
```

32. An isolated RNA molecule that functions as a protein transcriptional activation domain, wherein the RNA molecule comprises a sequence having at least 80% homology with the sequence set forth as GGAUGCCUAAGCCUCUU (SEQ ID NO: 22).

33. An isolated transcriptional regulator comprising an RNA molecule comprising a sequence selected from the group consisting of:

```
                                                        (SEQ ID NO: 23)
m26-10    CGCGGAAGAAUGAUCCCCCAAGUGGAUGCCUAAGCCUCUU;

(SEQ ID NO: 24)
m26-36    CGCGGAAGAAUUCUCCCCCAAGUGGAUGCCUAAGCCUCUU;

(SEQ ID NO: 25)
m26-31    CGCGGAAGAAUGCUCCCCCGAGUGGAUGCCUAAGCCUCAU;

(SEQ ID NO: 26)
m26-9     CGCGGAGGAAUGCUCCCCCGAGUGGAUGCCUAAUCCUCUU;

(SEQ ID NO: 27)
m26-14    CGCGGAAGCAUACUCCCCCGAGUGGAUGCCUAAGCCUCUU;

(SEQ ID NO: 28)
m26-15    CGCGGACCAAUGGUCCCCCAAGUGGAUGCCUAAGCCUCUU;

(SEQ ID NO: 29)
m26-34    CGCGGAAGAUUGCCCCCCAAGUGGAUGCCUAAACCUCUA;

(SEQ ID NO: 30)
m26-29    CGCGGAAGAUUGUUCCCCCAAGUGGAUGCCUAAACCUCAU;

(SEQ ID NO: 31)
m26-28    CGCGGAAAAAUACUCCCCCAAGUGGAUGCCUAAACCUAUU;

(SEQ ID NO: 32)
m26-17    CGCGGAAGAAUGAUCCCCCAGGUGGAUGCCUAAGCCUCUA;

(SEQ ID NO: 33)
m26-30    CGCGGAACAAUGCUCCCCCAGCUGGAUGCCUAAGCCUCUA;

(SEQ ID NO: 34)
m26-20    CGGGGAAGAAUGCUGCCCAAAGUGGAUGCCUAAGCCUCUU;

(SEQ ID NO: 35)
m26-4     CGCGGAAGAAUGCUGCCCAACCUGGAUGCCUAAACCUCUU;

(SEQ ID NO: 36)
m26-32    CGCGGAAGAAUGCUGCCCAACCUGGAUGCCUAAACCUCUU;

(SEQ ID NO: 37)
m26-13    CUCGGAACAAUGCCCCCCAAGUGGAUGCCUAAACCUCAU;

(SEQ ID NO: 38)
m26-35    CUCGGAAGAAUUCUCCCGAUAGUGGAUGCCUAAGCCUCUU;

(SEQ ID NO: 39)
m26-16    CGCGGAAGAAGAGUCCCCCGAGUGGAUGCCUAAACCUCUU;

(SEQ ID NO: 40)
m26-18    CGCGGAACAAUGUUGCCCCAAAUGGAUGCCUAAGCCUCUU;

(SEQ ID NO: 41)
m26-25    CGCGGAAGAACACUCCCCCACGUGGAUGCCUAAGCCUCCUU;

(SEQ ID NO: 42)
m26-21    CGCGGAAGACUGCAGCCCCAGGUGGAUGCCUAAACCUCGGU;

(SEQ ID NO: 43)
m26-39    CCCGGAAGACUGCAGCCCCAGGUGGAUGCCUAAACCUCUU;

(SEQ ID NO: 44)
m26-33    CGCGGAAGACUUCAGCCCCAAGUGGAUGCCUAAGCCUCUUA;

(SEQ ID NO: 45)
m26-1     CGCGGGUGUAAGCCCCCCAGGUGGAUGCCUAAGCCUCUU;

(SEQ ID NO: 46)
m26-23    CGCGUAAACAUGCGGCCCCAAGUGGAUGCCUAAGCCUCCU;

(SEQ ID NO: 47)
m26-24    CGCGGAAAGAUGAUCACCCGAGUGGAUGCCUAAGCCUCUU;

(SEQ ID NO: 48)
m26-11    CGCGCGAGUAUACUCCCCCAAGCGGAUGCCUAAGCCUCUU;

(SEQ ID NO: 49)
m26-19    CGCAGAAGAUACCUCCCCCAAGUGGAUGCCUAAGCCUCAU;

(SEQ ID NO: 50)
m26-26    AACAGAAGAAUACUCCCCCAAGUGGAUACCUAAGCAUCUU;

(SEQ ID NO: 51)
m26-37    CGCGGAAAAAUUCUUCCCCCAAGUGGAUGCCUAAGCCUCUU;

(SEQ ID NO: 52)
m26-38    CGCGGAAAAAUUCUUCCCCCAAGUGGAUGCGUAAGCCUCUU;

(SEQ ID NO: 53)
m26-7     CGCGGAAGAACGCUCCCCGACGUGGAUGCCUAUUGUCCUU;
and
                                                        (SEQ ID NO: 54)
con-      CGCGGAAGAAUGCUCCCCCAAGUGGAUGCCUAAGCCUCUU.
sensus
```

34. The isolated transcriptional regulator of claim 33 comprising an RNA molecule comprising the sequence of:

```
consensus                                               (SEQ ID NO: 54)
CGCGGAAGAAUGCUCCCCCAAGUGGAUGCCUAAGCCUCUU.
```

35. The isolated transcriptional regulator of claim 33 comprising an RNA molecule comprising the sequence of:

CGCGGAAGAUUGUUCCCCCAAGUGGAUGCCUAAACCUCAU (m26-12). (SEQ ID NO: 30)

36. The isolated transcriptional regulator of claim 33 further comprising at least one MS2 hairpin.

37. The isolated transcriptional regulator of claim 33 further comprising at least two MS2 hairpins.

38. The isolated transcriptional regulator of claim 33 further comprising an Iron Response Element (IRE).

39. The isolated transcriptional regulator of claim 33 further comprising a fusion of an Iron Response Element (IRE) and an MS2 hairpin.

40. The isolated transcriptional regulator of claim 33 further comprising a RPR terminator.

41. The isolated transcriptional regulator of claim 33, further comprising a DNA binding moiety, wherein the DNA binding moiety is a LexA-MS2 fusion protein.

42. A transcriptional regulatory system comprising:
an isolated transcriptional regulator comprising an RNA molecule comprising a sequence having at least 80% homology with the sequence set forth as GGAUGCCUAAGCCUCUU (SEQ ID NO: 22);
a DNA-binding protein; and
a DNA template.

43. The transcriptional regulatory system of claim 42 further comprising transcriptional machinery.

44. The transcriptional regulatory system of claim 43, wherein the transcriptional machinery comprises RNA polymerase.

* * * * *

SEQUENCE LISTING

```
<160> NUMBER OF SEQ ID NOS: 107

<210> SEQ ID NO 1
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 1
uugugagcug gccucccgcg auggggauaa cgccacugaa                            40

<210> SEQ ID NO 2
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 2 cugguccccgu cucgcggcgc ccuagcgcag uaauucuuca                           40

<210> SEQ ID NO 3
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 3
auuuacagcg cgggccgcug uuugugucua guggccuuga                            40

<210> SEQ ID NO 4
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator
```

-continued

```
<400> SEQUENCE: 4
cgucgcaagc cggucuugcg ucaugggccu gaggaauucg                             40

<210> SEQ ID NO 5
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 5
acggcauacc ugcuggggggg gcggggcugg cccucgucgu                            40

<210> SEQ ID NO 6
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 6
ggcgccaagc uggucuuaug cgcuagcuug gggggccacc                             40

<210> SEQ ID NO 7
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 7
guauuucgcc cggacgugcg auuggguggcu ggccaucauu                            40

<210> SEQ ID NO 8
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 8
gaucgcauaa caugggcgau ugguucugcu ggucagacca                             40

<210> SEQ ID NO 9
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 9
gauuuaugcc cccuccggag cuaugcauga gcgggccucu                             40

<210> SEQ ID NO 10
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 10
```

```
cgcggaagaa ugcuccccca aguggaugcc uaagccucuu                              40
```

<210> SEQ ID NO 11
<211> LENGTH: 39
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 11

```
guuacagcgc gggccgcugu cuguaucuau uggccgugg                               39
```

<210> SEQ ID NO 12
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 12

```
ggcgucaagc uggucuuaug agcuagcugg gggggccacc                              40
```

<210> SEQ ID NO 13
<211> LENGTH: 41
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 13

```
ggcgccaagc uggucuuaug cgcuagcgug ggguggccac c                            41
```

<210> SEQ ID NO 14
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 14

```
aacgccaagc uggucuuaag ugucgccuug gggagccaca                              40
```

<210> SEQ ID NO 15
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 15

```
ggcgaaaagc uggucuugug cucuggaaug gugggccacc                              40
```

<210> SEQ ID NO 16
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 16

```
cgcccuaagc uggucuuagg cgccggcuug cggggccacc                              40
```

```
<210> SEQ ID NO 17
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 17
cgcgccgagc gggucuugag cgcaaggaug gacuaccgcc                                 40

<210> SEQ ID NO 18
<211> LENGTH: 41
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 18
ggggccgagc cggucucgug cccaagcaag gggugccacc c                               41

<210> SEQ ID NO 19
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 19
ggcgccaggc agguccugug cguuagccug uggggccacc                                 40

<210> SEQ ID NO 20
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 20
ggcgcgaagc uggucuuuug cgccugcuua gggagcgacc                                 40

<210> SEQ ID NO 21
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 21
agugccaagc uggccuuaug cacuaccuuc cggcgccacg                                 40

<210> SEQ ID NO 22
<211> LENGTH: 17
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 22
ggaugccuaa gccucuu                                                          17

<210> SEQ ID NO 23
```

```
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 23
cgcggaagaa ugauccccca aguggaugcc uaagccucuu                              40

<210> SEQ ID NO 24
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 24
cgcggaagaa uucuccccca aguggaugcc uaagccucuu                              40

<210> SEQ ID NO 25
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 25
cgcggaagaa ugcucccccg aguggaugcc uaagccucau                              40

<210> SEQ ID NO 26
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 26
cgcggaggaa ugcuccccccg aguggaugcc uaauccucuu                             40

<210> SEQ ID NO 27
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 27
cgcggaagca uacuccccg aguggaugcc uaagccucuu                               40

<210> SEQ ID NO 28
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 28
cgcggaccaa uggucccccca aguggaugcc uaagccucuu                             40

<210> SEQ ID NO 29
<211> LENGTH: 40
<212> TYPE: RNA
```

```
<213> ORGANISM: Artificial sequence
<220> FEATURE:
<223> OTHER INFORMATION: Transcriptional activating sequence of an
      RNA-based transcriptional regulator

<400> SEQUENCE: 29
cgcggaagau ugccccccca aguggaugcc uaaaccucua                            40

<210> SEQ ID NO 30
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 30
cgcggaagau uguccccca aguggaugcc uaaaccucau                             40

<210> SEQ ID NO 31
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 31
cgcggaaaaa uacuccccca aguggaugcc uaaaccuauu                            40

<210> SEQ ID NO 32
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 32
cgcggaagaa ugauccccca gguggaugcc uaagccucua                            40

<210> SEQ ID NO 33
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 33
cgcggaacaa ugcuccccca gcuggaugcc uaagccucua                            40

<210> SEQ ID NO 34
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 34
cggggaagaa ugcugcccaa aguggaugcc uaagccucuu                            40

<210> SEQ ID NO 35
<211> LENGTH: 40
<212> TYPE: RNA
<213> ORGANISM: Artificial sequence
<220> FEATURE:
```

<223> OTHER INFORMATION: Transcriptional activating sequence of an
      RNA-based transcriptional regulator

<400> SEQUENCE: 35
cgcggaagaa ugcugcccaa ccuggaugcc uaaaccucuu                    40

<210> SEQ ID NO 36
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 36
cgcggaagaa ugcugcccaa ccuggaugcc uaaaccucuu                    40

<210> SEQ ID NO 37
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 37
cucggaacaa ugcccccca aguggaugcc uaaaccucau                    40

<210> SEQ ID NO 38
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 38
cucggaagaa uucucccgau aguggaugcc uaagccucuu                    40

<210> SEQ ID NO 39
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 39
cgcggaagaa gagucccccg aguggaugcc uaaaccucuu                    40

<210> SEQ ID NO 40
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 40
cgcggaacaa uguugcccca aauggaugcc uaagccucuu                    40

<210> SEQ ID NO 41
<211> LENGTH: 41
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 41
cgcggaagaa cacuccccca cguggaugcc uaagccuccu u            41

<210> SEQ ID NO 42
<211> LENGTH: 41
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 42
cgcggaagac ugcagcccca gguggaugcc uaaaccucgg u            41

<210> SEQ ID NO 43
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 43
cccggaagac ugcagcccca gguggaugcc uaaaccucuu             40

<210> SEQ ID NO 44
<211> LENGTH: 41
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 44
cgcggaagac uucagcccca aguggaugcc uaagccucuu a            41

<210> SEQ ID NO 45
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 45
cgcgggugua agccccccca gguggaugcc uaagccucuu             40

<210> SEQ ID NO 46
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 46
cgcguaaaca ugcggcccca aguggaugcc uaagccuccu             40

<210> SEQ ID NO 47
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 47
cgcggaaaga ugaucacccg aguggaugcc uaagccucuu        40

<210> SEQ ID NO 48
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 48
cgcgcgagua uacucccca agcggaugcc uaagccucuu        40

<210> SEQ ID NO 49
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 49
cgcagaagau accuccccca aguggaugcc uaagccucau        40

<210> SEQ ID NO 50
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 50
aacagaagaa uacuccccca aguggauacc uaagcaucuu        40

<210> SEQ ID NO 51
<211> LENGTH: 41
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 51
cgcggaaaaa uucuucccccc aaguggaugc cuaagccucu u        41

<210> SEQ ID NO 52
<211> LENGTH: 41
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 52
cgcggaaaaa uucuucccccc aaguggaugc guaagccucu u        41

<210> SEQ ID NO 53
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 53
cgcggaagaa cgcuccccga cguggaugcc uauugccuu        40

<210> SEQ ID NO 54
<211> LENGTH: 40
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 54
cgcggaagaa ugcuccccca aguggaugcc uaagccucuu                               40

<210> SEQ ID NO 55
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 55 gggggggat cccagccagt cgccgttgcg aat                                      33

<210> SEQ ID NO 56
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 56 ggggggcta gcatgaaagc gttaacggcc agg                                      33

<210> SEQ ID NO 57
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 57
ccgccgggat ccgctccccc gaccgatgtc agc                                     33

<210> SEQ ID NO 58
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 58
ccgccgctcg agttaaccgt actcgtcaat tccaag                                  36

<210> SEQ ID NO 59
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 59
ccgcggacta gtatgaaagc gttaacggcc aggc                                    34

<210> SEQ ID NO 60
<211> LENGTH: 24
<212> TYPE: RNA
<213> ORGANISM: Artificial sequence
<220> FEATURE:

```
<223> OTHER INFORMATION: Transcriptional activating sequence of an
      RNA-based transcriptional regulator

<400> SEQUENCE: 60
cccaagugga ugccuaagcc ucuu                                              24

<210> SEQ ID NO 61
<211> LENGTH: 50
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 61
cgacuggcga gagccaggua acgaauccug gguggaugcc uaagccucuu                  50

<210> SEQ ID NO 62
<211> LENGTH: 50
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 62
cgacuggcga gagccaggua acgaauccgg gcaggaugcc uaagccucuu                  50

<210> SEQ ID NO 63
<211> LENGTH: 51
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 63
cgacuggcga gagccaggua acgaauccuu acgcggaugc cuaagccucu u                51

<210> SEQ ID NO 64
<211> LENGTH: 50
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 64
cgacuggcga gagccaggua acgaauccua accggaugcc uaagccucuu                  50

<210> SEQ ID NO 65
<211> LENGTH: 50
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 65
cgacuggcga gagccaggua acgaauccca accggaugcc uaagccucuu                  50

<210> SEQ ID NO 66
<211> LENGTH: 50
<212> TYPE: RNA
<213> ORGANISM: Artificial sequence
<220> FEATURE:
<223> OTHER INFORMATION: Transcriptional activating sequence of an
      RNA-based transcriptional regulator
```

<400> SEQUENCE: 66
cgacuggcga gagccaggua aagaauccua accggaugcc uaagccucuu        50

<210> SEQ ID NO 67
<211> LENGTH: 50
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 67
cgacuggcga gagccaggua ccgaauccua accggaugcc uaagccucuu        50

<210> SEQ ID NO 68
<211> LENGTH: 79
<212> TYPE: DNA
<213> ORGANISM: Artificial sequence
<220> FEATURE:
<223> OTHER INFORMATION: Synthetic degenerative oligonucleotide
<220> FEATURE:
<221> NAME/KEY: misc_feature
<222> LOCATION: (30)..(36)
<223> OTHER INFORMATION: wherein n is a, c, g, t or u.

<400> SEQUENCE: 68
cgcgcggcat gcaagaggct taggcatccn nnnnnnattc gttacctggc tctcgccagt        60
cgcccgggac gccgacgcc                                                    79

<210> SEQ ID NO 69
<211> LENGTH: 24
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 69
cccaagcgga ugccuaagcc ucuu                                    24

<210> SEQ ID NO 70
<211> LENGTH: 26
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 70
cgacuggcga gagccaggua acgaau                                  26

<210> SEQ ID NO 71
<211> LENGTH: 24
<212> TYPE: RNA
<213> ORGANISM: Artificial sequence
<220> FEATURE:
<223> OTHER INFORMATION: Transcriptional activating sequence of an
      RNA-based transcriptional regulator

<400> SEQUENCE: 71
cccaaccgga ugccuaagcc ucuu                                    24

<210> SEQ ID NO 72
<211> LENGTH: 40
<212> TYPE: DNA
<213> ORGANISM: Artificial sequence

```
<220> FEATURE:
<223> OTHER INFORMATION: Transcriptional activating sequence

<400> SEQUENCE: 72
cgcggaagaa tgatccccca agtggatgcc taagcctctt                              40

<210> SEQ ID NO 73
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 73
cgcggaagaa ttctccccca agtggatgcc taagcctctt                              40

<210> SEQ ID NO 74
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 74
cgcggaagaa tgctcccccg agtggatgcc taagcctcat                              40

<210> SEQ ID NO 75
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 75
cgcggaggaa tgctcccccg agtggatgcc taatcctctt                              40

<210> SEQ ID NO 76
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 76
cgcggaagca tactcccccg agtggatgcc taagcctctt                              40

<210> SEQ ID NO 77
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 77
cgcggaccaa tggtccccca agtggatgcc taagcctctt                              40

<210> SEQ ID NO 78
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 78
cgcggaagat tgccccccca agtggatgcc taaacctcta                              40
```

```
<210> SEQ ID NO 79
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 79
cgcggaagat tgttccccca agtggatgcc taaacctcat                          40

<210> SEQ ID NO 80
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 80
cgcggaaaaa tactccccca agtggatgcc taaacctatt                          40

<210> SEQ ID NO 81
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 81
cgcggaagaa tgatccccca ggtggatgcc taagcctcta                          40

<210> SEQ ID NO 82
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 82
cgcggaacaa tgctccccca gctggatgcc taagcctcta                          40

<210> SEQ ID NO 83
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 83
cggggaagaa tgctgcccaa agtggatgcc taagcctctt                          40

<210> SEQ ID NO 84
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 84
cgcggaagaa tgctgcccaa cctggatgcc taaacctctt                          40

<210> SEQ ID NO 85
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 85
```
cgcggaagaa tgctgcccaa cctggatgcc taaacctctt                    40

<210> SEQ ID NO 86
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 86
ctcggaacaa tgcccccca agtggatgcc taaacctcat                     40

<210> SEQ ID NO 87
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 87
ctcggaagaa ttctcccgat agtggatgcc taagcctctt                    40

<210> SEQ ID NO 88
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 88
cgcggaagaa gagtcccccg agtggatgcc taaacctctt                    40

<210> SEQ ID NO 89
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 89
cgcggaacaa tgttgcccca aatggatgcc taagcctctt                    40

<210> SEQ ID NO 90
<211> LENGTH: 41
<212> TYPE: DNA
<213> ORGANISM: Artificial sequence
<220> FEATURE:
<223> OTHER INFORMATION: Transcriptional activating sequence

<400> SEQUENCE: 90
cgcggaagaa cactccccca cgtggatgcc taagcctcct t                  41

<210> SEQ ID NO 91
<211> LENGTH: 41
<212> TYPE: DNA
<213> ORGANISM: Artificial sequence
<220> FEATURE:
<223> OTHER INFORMATION: Transcriptional activating sequence

<400> SEQUENCE: 91
cgcggaagac tgcagcccca ggtggatgcc taaacctcgg t                  41

<210> SEQ ID NO 92
<211> LENGTH: 40
<212> TYPE: DNA
<213> ORGANISM: Artificial sequence

```
<220> FEATURE:
<223> OTHER INFORMATION: Transcriptional activating sequence

<400> SEQUENCE: 92
cccggaagac tgcagcccca ggtggatgcc taaacctctt                              40

<210> SEQ ID NO 93
<211> LENGTH: 41
<212> TYPE: DNA
<213> ORGANISM: Artificial sequence
<220> FEATURE:
<223> OTHER INFORMATION: Transcriptional activating sequence

<400> SEQUENCE: 93
cgcggaagac ttcagcccca agtggatgcc taagcctctt a                            41

<210> SEQ ID NO 94
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 94
cgcgggtgta agccccccca ggtggatgcc taagcctctt                              40

<210> SEQ ID NO 95
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 95
cgcgtaaaca tgcggcccca agtggatgcc taagcctcct                              40

<210> SEQ ID NO 96
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 96
cgcggaaaga tgatcacccg agtggatgcc taagcctctt                              40

<210> SEQ ID NO 97
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 97
cgcgcgagta tactcccca agcggatgcc taagcctctt                               40

<210> SEQ ID NO 98
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 98 cgcagaaagat acctcccca agtggatgcc taagcctcat                              40
```

```
<210> SEQ ID NO 99
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 99
aacagaagaa tactccccca agtggatacc taagcatctt                                40

<210> SEQ ID NO 100
<211> LENGTH: 41
<212> TYPE: DNA
<213> ORGANISM: Artificial sequence
<220> FEATURE:
<223> OTHER INFORMATION: Transcriptional activating sequence

<400> SEQUENCE: 100
cgcggaaaaa ttcttccccc aagtggatgc ctaagcctct t                              41

<210> SEQ ID NO 101
<211> LENGTH: 41
<212> TYPE: DNA
<213> ORGANISM: Artificial sequence
<220> FEATURE:
<223> OTHER INFORMATION: Transcriptional activating sequence

<400> SEQUENCE: 101
cgcggaaaaa ttcttccccc aagtggatgc gtaagcctct t                              41

<210> SEQ ID NO 102
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 102
cgcggaagaa cgctccccga cgtggatgcc tattgtcctt                                40

<210> SEQ ID NO 103
<211> LENGTH: 40
<212> TYPE: DNA
<213> ORGANISM: Artificial sequence
<220> FEATURE:
<223> OTHER INFORMATION: Transcriptional activating sequence

<400> SEQUENCE: 103
cgcggaagaa tgctccccca agtggatgcc taagcctctt                                40

<210> SEQ ID NO 104
<211> LENGTH: 100
<212> TYPE: RNA
<213> ORGANISM: Artificial sequence
<220> FEATURE:
<223> OTHER INFORMATION: Transcriptional Activator

<400> SEQUENCE: 104
uuccggcuag aacuagugga uccccgggc gcgcgaguau acuccccaa gcggaugccu            60 aagccucuug caugccuagg ucgacucuag aggaucggaa                                100

<210> SEQ ID NO 105
<211> LENGTH: 38
<212> TYPE: RNA
<213> ORGANISM: Artificial sequence
<220> FEATURE:
<223> OTHER INFORMATION: TMR aptamer
```

```
<400> SEQUENCE: 105
ggaucccgac uggcgagagc cagguaacga auggaucc                            38

<210> SEQ ID NO 106
<211> LENGTH: 110
<212> TYPE: RNA
<213> ORGANISM: Artificial sequence
<220> FEATURE:
<223> OTHER INFORMATION: Transcriptional activator (clone 96)

<400> SEQUENCE: 106
uuccggcuag aacuagugga uccccgggc gacuggcgag agccagguaa cgaauccuaa     60
ccggaugccu aagccucuug caugccuagg ucgacucuag aggaucggaa              110

<210> SEQ ID NO 107
<211> LENGTH: 40
<212> TYPE: DNA
<213> ORGANISM: Artificial sequence
<220> FEATURE:
<223> OTHER INFORMATION: Transcriptional activating sequence of an
      RNA-based transcriptional regulator

<400> SEQUENCE: 107
cgcggaagaa tgctccccca agtggatgcc taagcctctt                          40
```